(12) United States Patent
Shuto

(10) Patent No.: US 6,664,214 B1
(45) Date of Patent: Dec. 16, 2003

(54) URACIL COMPOUNDS AND USE THEREOF

(75) Inventor: Akira Shuto, Kobe (JP)

(73) Assignee: Sumitomo Chemical Company, Limited, Osaka (JP)

(*) Notice: Subject to any disclaimer, the term of this patent is extended or adjusted under 35 U.S.C. 154(b) by 24 days.

(21) Appl. No.: 10/019,950

(22) PCT Filed: Jun. 23, 2000

(86) PCT No.: PCT/JP00/04163

§ 371 (c)(1),
(2), (4) Date: Jan. 7, 2002

(87) PCT Pub. No.: WO01/04101

PCT Pub. Date: Jan. 18, 2001

(30) Foreign Application Priority Data

Jul. 7, 1999 (JP) .............................................. 11/193361
Mar. 24, 2000 (JP) .......................................... 2000/083966

(51) Int. Cl.$^7$ .............................................. A01N 43/54
(52) U.S. Cl. ........................ 504/243; 544/312; 544/314
(58) Field of Search ........................ 504/243; 544/312, 544/314

(56) References Cited

U.S. PATENT DOCUMENTS

| | | | |
|---|---|---|---|
| 4,859,229 A | 8/1989 | Wenger et al. | 544/309 |
| 5,084,084 A | 1/1992 | Satow et al. | 544/309 |
| 5,127,935 A | 7/1992 | Satow et al. | 544/309 |
| 5,399,543 A | 3/1995 | Theodoridis | 544/309 |
| 5,567,670 A | 10/1996 | Amuti et al. | 504/230 |
| 5,602,077 A | 2/1997 | Amuti et al. | 544/313 |
| 5,674,810 A | 10/1997 | Theodoridis | 504/136 |
| 5,714,437 A | 2/1998 | Takano et al. | 504/238 |
| 5,798,316 A | 8/1998 | Theodoridis | 504/136 |

FOREIGN PATENT DOCUMENTS

| | | |
|---|---|---|
| EP | 705829 | 4/1996 |
| EP | 255047 | 2/1998 |
| JP | 5-39272 | 2/1993 |
| JP | 9-241245 | 9/1997 |
| WO | WO 95/17096 | 6/1995 |
| WO | WO 97/01541 | 1/1997 |
| WO | WO 97/05116 | 2/1997 |
| WO | WO 99/21837 | 5/1999 |

Primary Examiner—John M. Ford
(74) Attorney, Agent, or Firm—Birch Stewart Kolasch & Birch LLP

(57) ABSTRACT

The invention provides an uracil compound represented by the general formula:

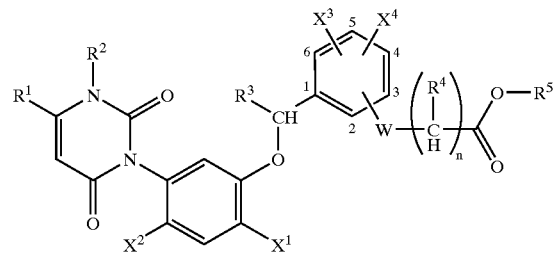

wherein W represents oxygen or sulfur; $R^1$ represents $C_1$- to $C_3$-alkyl or $C_1$- to $C_3$-haloalkyl; $R^2$ represents $C_1$- to $C_3$-alkyl or $C_1$- to $C_3$-haloalkyl; $R^3$ represents hydrogen, $C_1$- to $C_3$-alkyl, phenyl, $C_1$- to $C_3$-haloalkyl or cyano; $R^4$ represents hydrogen or $C_1$- to $C_3$-alkyl; $R^5$ represents $C_1$- to $C_6$-alkyl, $C_1$- to $C_6$-haloalkyl, $C_3$- to $C_6$-alkenyl, $C_3$- to $C_6$-haloalkenyl, $C_3$- to $C_6$-alkynyl or $C_3$- to $C_6$-haloalkynyl; $X^1$ represents halogen; $X^2$ represents hydrogen or halogen; $X^3$ and $X^4$ are independent with each other and each represents hydrogen, halogen, $C_1$- to $C_6$-alkyl, $C_1$- to $C_6$-haloalkyl, $C_2$- to $C_6$-alkenyl, $C_2$- to $C_6$-haloalkenyl, $C_3$- to $C_6$-alkynyl, $C_3$- to $C_6$-haloalkynyl, $C_1$- to $C_6$-alkoxy-$C_1$- to $C_6$-alkyl, $C_1$- to $C_6$-alkoxy, $C_1$- to $C_6$-haloalkoxy or cyano; and n represents an integer of 1 to 4. The uracil compound has an excellent herbicidal effect against various weeds and therefore it is useful as an active ingredient for a herbicide.

13 Claims, No Drawings

URACIL COMPOUNDS AND USE THEREOF

This application is the national phase under 35 U.S.C. §371 of PCT International Application No. PCT/JP00/04163 which has an International filing date of Jun. 23, 2000, which designated the United States of America.

TECHNICAL FIELD

The present invention relates to uracil compounds and use thereof.

DISCLOSURE OF INVENTION

The subject of the invention is to provide compounds having an excellent herbicidal activity.

As the result of extensive studies conducted for finding out compounds having an excellent herbicidal activity, the inventors of the invention have found the fact that uracil compounds represented by Chemical Formula 2, shown below, have an excellent herbicidal activity and have completed the invention. Therefore, the invention provides an uracil compound (hereinafter, referred to as the compound (s) of the invention) represented by Chemical Formula 2:

[Chemical Formula 2]

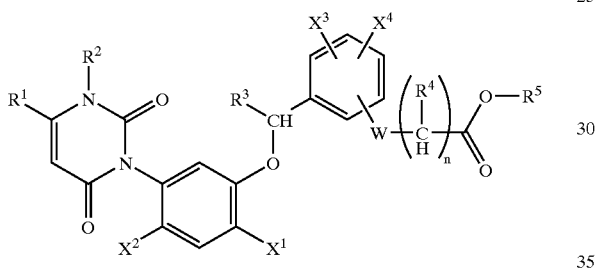

wherein W represents oxygen or sulfur; $R^1$ represents $C_1$- to $C_3$-alkyl or $C_1$- to $C_3$-haloalkyl; $R^2$ represents $C_1$- to $C_3$-alkyl or $C_1$- to $C_3$-haloalkyl; $R^3$ represents hydrogen, $C_1$- to $C_3$-alkyl, phenyl, $C_1$- to $C_3$-haloalkyl or cyano; $R^4$ represents hydrogen or $C_1$- to $C_3$-alkyl; $R^5$ represents $C_1$- to $C_6$-alkyl, $C_1$- to $C_6$-haloalkyl, $C_3$- to $C_6$-alkenyl, $C_3$- to $C_6$-haloalkenyl, $C_3$- to $C_6$-alkynyl or $C_3$- to $C_6$-haloalkynyl; $X^1$ represents halogen; $X^2$ represents hydrogen or halogen; $X^3$ and $X^4$ are independent with each other and each represents hydrogen, halogen, $C_1$- to $C_6$-alkyl, $C_1$- to $C_6$-haloalkyl, $C_2$- to $C_6$-alkenyl, $C_2$- to $C_6$-haloalkenyl, $C_3$- to $C_6$-alkynyl, $C_3$- to $C_6$-haloalkynyl, $C_1$- to $C_6$-alkoxy-$C_1$- to $C_6$-alkyl, $C_1$- to $C_6$-alkoxy, $C_1$- to $C_6$-haloalkoxy or cyano; and n represents an integer of 1 to 4; and a herbicide comprising the same as an active ingredient.

BEST MODE FOR CARRYING OUT THE INVENTION

In the invention, $C_1$- to $C_3$-alkyl represented by $R^1$ means methyl, ethyl, propyl or isopropyl; $C_1$- to $C_3$-haloalkyl represented by $R^1$ includes bromomethyl, chloromethyl, fluoromethyl, dichloromethyl, trichloromethyl, difluoromethyl, trifluoromethyl, pentafluoroethyl, 1,1-difluoroethyl, 3,3,3-trifluoropropyl and the like;

$C_1$- to $C_3$-alkyl represented by $R^2$ means methyl, ethyl, propyl or isopropyl; $C_1$- to $C_3$-haloalkyl represented by $R^2$ includes bromomethyl, chloromethyl, fluoromethyl, dichloromethyl, trichloromethyl, difluoromethyl, chlorodifluoromethyl, bromodifluoromethyl, trifluoromethyl, pentafluoroethyl, 1,1-difluoroethyl, 3,3,3-trifluoropropyl and the like;

$C_1$- to $C_3$-alkyl represented by $R^3$ means methyl, ethyl, propyl or isopropyl; $C_1$- to $C_3$-haloalkyl represented by $R^3$ includes bromomethyl, chloromethyl, fluoromethyl, dichloromethyl, trichloromethyl, difluoromethyl, trifluoromethyl, pentafluoroethyl, 1,1-difluoroethyl, 3,3,3-trifluoropropyl and the like;

$C_1$- to $C_3$-alkyl represented by $R^4$ means methyl, ethyl, propyl or isopropyl; $C_1$- to $C_6$-alkyl represented by $R^5$ includes methyl, ethyl, propyl, isopropyl, butyl, s-butyl, t-butyl and the like; $C_1$- to $C_6$-haloalkyl represented by $R^5$ includes bromomethyl, chloromethyl, fluoromethyl, dichloromethyl, trichloromethyl, difluoromethyl, chlorodifluoromethyl, bromodifluoromethyl, pentafluoroethyl, 2-fluoroethyl, 2,2,2-trichloroethyl, 3,3,3-trifluoropropyl, 3,3,3-trichloropropyl and the like; $C_3$- to $C_6$-alkenyl represented by $R^5$ includes allyl, 1-methylallyl, 1,1-dimethylallyl, 2-methylallyl, 1-butenyl, 2-butenyl, 3-butenyl and the like; $C_3$- to $C_6$-haloalkenyl represented by $R^5$ includes 1-chloroallyl, 1-bromoallyl, 2-chloroallyl, 3,3-dichloroallyl and the like; $C_3$- to $C_6$-alkynyl represented by $R^5$ includes 2-propynyl, 1-methyl-2-propynyl, 1,1-dimethyl-2-propynyl, 2-butynyl, 3-butynyl, 1-methyl-2-butynyl and the like; $C_3$- to $C_6$-haloalkynyl represented by $R^5$ includes 3-chloro-2-propynyl, 3-bromo-2-propynyl, 1-fluoro-2-propynyl, 1-chloro-2-propynyl, 1-bromo-2-propynyl, 1-chloro-2-butynyl and the like;

halogen represented by $X^1$ and $X^2$ means fluorine, chlorine, bromine and iodine; halogen represented by $X^3$ and $X^4$ means fluorine, chlorine, bromine and iodine; $C_1$- to $C_6$-alkyl represented by $X^3$ and $X^4$ includes methyl, ethyl, propyl, isopropyl, butyl, s-butyl, t-butyl and the like; $C_1$- to $C_6$-haloalkyl represented by $X^3$ and $X^4$ includes bromomethyl, chloromethyl, fluoromethyl, dichloromethyl, trichloromethyl, difluoromethyl, chlorodifluoromethyl, bromodifluoromethyl, trifluoromethyl, pentafluoroethyl, 2-fluoroethyl, 1,1-difluoroethyl, 2,2,2-trichloroethyl, 3,3,3-trifluoropropyl, 3,3,3-trichloropropyl and the like; $C_2$- to $C_6$-alkenyl represented by $X^3$ and X4 includes vinyl, allyl, 1-methylallyl, 1,1-dimethylallyl, 2-methylallyl, 1-butenyl, 2-butenyl, 3-butenyl and the like; $C_2$- to $C_6$-haloalkenyl represented by $X^3$ and $X^4$ includes difluorovinyl dichlorovinyl, 1-chloroallyl, 1-bromoallyl, 2-chloroallyl, 3,3-dichloroallyl and the like; $C_3$- to $C_6$-alkynyl represented by $X^3$ and $X^4$ includes 2-propynyl, 1-methyl-2-propynyl, 1,1-dimethyl-2-propynyl, 2-butynyl, 3-butynyl, 1-methyl-2-butynyl and the like; $C_3$- to $C_6$-haloalkynyl represented by $X^3$ and $X^4$ includes 3-chloro-2-propynyl, 3-bromo-2-propynyl, 1-fluoro-2-propynyl, 1-chloro-2-propynyl, 1-bromo-2-propynyl, 1-chloro-2-butynyl and the like; $C_1$- to $C_6$-alkoxy-$C_1$- to $C_6$-alkyl represented by $X^3$ and $X^4$ includes methoxymethyl, 2-methoxyethyl, 1-methoxyethyl, 3-methoxypropyl, ethoxymethyl, 2-ethoxyethyl, 3-ethoxypropyl, isopropoxymethyl, 2-isopropoxyethyl and the like; $C_1$- to $C_6$-alkoxy represented by $X^3$ and $X^4$ includes methoxy, ethoxy, propoxy, isopropoxy, butyloxy, s-butyloxy, t-butyloxy and the like; and $C_1$- to $C_6$-haloalkoxy represented by $X^3$ and $X^4$ includes chloromethoxy, bromomethoxy, dichloromethyloxy, trichloromethyloxy, trifluoromethyloxy, 2-fluoroethyloxy, 2,2,2-trichloroethyloxy and the like.

From the viewpoint of herbicidal activity, preferred compounds among the compounds of the invention are compounds wherein R¹ is methyl substituted with one or more fluorine (for example, trifluoromethyl, chlorodifluoromethyl, difluoromethyl or the like) or ethyl substituted with one or more fluorine (for example, pentafluoroethyl, 1,1-difluoroethyl or the like), compounds wherein $R^2$ is methyl, compounds wherein $X^1$ is chlorine, compounds wherein $X^2$ is fluorine, or compounds wherein the connecting position of W is 3- or 4-position on the benzene ring. A more preferred compound is methyl 2-[4-({2-chloro-4-fluoro-5-[3-methyl-2,6-dioxo-4-(trifluoromethyl)-1,2,3,6-tetrahydropyrimidine-1-yl]phenoxy}methyl)phenoxy]propionate.

While sometimes geometrical isomers originated from a double bond, optical isomers and diastereoisomers originated from (an) asymmetric carbon(s) may exist in the compounds of the invention, the compounds of the invention extends to all of these isomers and mixtures thereof.

Processes for producing the compound of the invention are described below.

The compound of the invention can be produced according to processes including (Production Process 1) to (Production Process 6) described below:

Production Process 1

The compound of the invention can be produced by reacting an uracil compound represented by Chemical Formula 3:

[Chemical Formula 3]

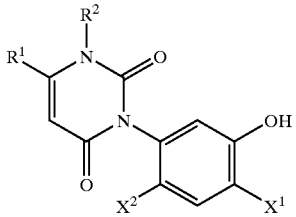

wherein $R^1$, $R^2$, $X^1$ and $X^2$ have the same meaning as above, with a compound represented by Chemical Formula 4:

[Chemical Formula 4]

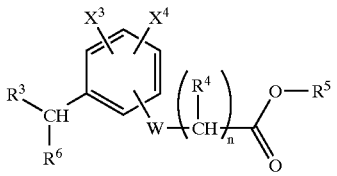

wherein $R^3$, $R^4$, $R^5$, W, $X^3$, $X^4$ and n have the same meaning as above and $R^6$ represents a leaving group such as chlorine, bromine, iodine, methanesulfonyloxy, p-toluenesulfonyloxy and the like, in the presence of a base.

Said reaction is usually carried out without solvent or in a solvent; the range of the reaction temperature is 0 to 200° C. and the range of the reaction period is usually a moment to 24 hours.

The amount of the reagents used for the reaction can optionally be varied according to circumstances, while the theoretical amount of the compound represented by Chemical Formula 4 is 1 mole and the amount of the base is 1 mole, based on 1 mole of the uracil compound represented by Chemical Formula 3.

Usable base includes organic bases such as pyridine, quinoline, benzyldimethylamine, phenethyldimethylamine, N-methylmorpholine, 1,8-diazabicyclo[5.4.0]undec-7-ene, 1,5-diazabicyclo[4.3.0]non-5-ene, 1,4-bicyclo[2.2.2]octane, 4-dimethylaminopyridine, N,N-dimethylaniline, N,N-diethylaniline, triethylamine, tri-n-propylamine, triisopropylamine, tri-n-butylamine, diisopropylethyalmine and the like; metal alkoxide such as sodium methoxide, sodium ethoxide, potassium t-butoxide and the like, and inorganic bases such as lithium carbonate, sodium carbonate, potassium carbonate, calcium carbonate, barium carbonate, lithium hydrogen carbonate, sodium hydrogen carbonate, potassium hydrogen carbonate, calcium hydrogen carbonate, barium hydrogen carbonate, sodium hydride, potassium carbonate, lithium hydroxide, sodium hydroxide, potassium hydroxide, calcium hydroxide, barium hydroxide and the like.

The solvent includes, for example, aliphatic hydrocarbons such as n-hexane, n-heptane, ligroin, cyclohexane, petroleum ether and the like; aromatic hydrocarbons such as benzene, toluene, xylene and the like; halogenated aromatic hydrocarbons such as chlorobenzene, dichlorobenzene, benzotrifluolide and the like; ethers such as diethyl ether, diisopropyl ether, methyl t-butyl ether, dioxane, tetrahydrofuran, ethylene glycol dimethyl ether and the like; ketones such as acetone, 2-butanone, methyl isobutyl ketone and the like; esters such as ethyl formate, ethyl acetate, butyl acetate, diethyl carbonate and the like; nitro compounds such as nitromethane, nitrobenzene and the like; nitriles such as acetonitrile, isobutyronitrile and the like; acid amides such as N,N-dimethylformamide, N,N-dimethylacetamide and the like; sulfur compounds such as dimethylsulfoxide, sulfolane and the like; alcohols such as methanol, ethanol, ethylene glycol, isopropanol, t-butanol and the like; and mixtures thereof.

After the reaction is completed, for example, the compound of the invention as desired can be obtained by treatments described in the following 1) or 2):

1) The reaction solution is poured into water, followed by extraction with an organic solvent, drying and concentration of the obtained organic layer.
2) The reaction solution is concentrated, or the reaction solution is filtered and the filtrate is concentrated.

The product obtained by the treatment 1) or 2) can be purified by a treatment such as chromatography, recrystallization or the like.

Production Process 2

The compound of the invention can be produced by reacting an uracil compound represented by Chemical Formula 3 described above with an alcohol compound represented by Chemical Formula 5:

[Chemical Formula 5]

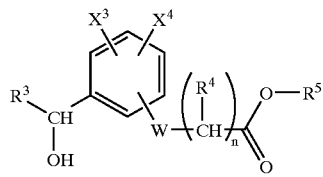

wherein $R^3$, $R^4$, $R^5$, W, $X^3$, $X^4$ and n have the same meaning as above, in the presence of a dehydrating agent.

The dehydrating agent includes, for example, a combination of a triarylphosphine such as triphenylphosphine and the like or a trialkylphosphine such as triethylphosphine and the like, and di(lower alkyl) azodicarboxylate such as diethyl azodicarboxylate, diisopropyl azodicarboxylate and the like.

Said reaction is usually carried out in a solvent; the range of the reaction temperature is −20 to 150° C., preferably 0 to 100° C., and the range of the reaction period is usually a moment to 48 hours.

The amount of the reagents used for the reaction is 1 to 3 moles, preferably 1 to 1.2 mole, for the alcohol compound represented by Chemical Formula 4; 1 to 3 moles, preferably 1 to 1.2 mole, for the triarylphosphine or trialkylphosphine; and 1 to 3 moles, preferably 1 to 1.2 mole, for the di(lower alkyl) azodicarboxylate, based on 1 mole of the uracil compound represented by Chemical Formula 3. The proportion of these reagents can optionally be varied according to circumstances.

The solvent used in the invention includes aliphatic hydrocarbons such as n-hexane, n-heptane, ligroin, cyclohexane, petroleum ether and the like; aromatic hydrocarbons such as benzene, toluene, xylene and the like; halogenated aromatic hydrocarbons such as chlorobenzene, dichlorobenzene, benzotrifluolide and the like; ethers such as diethyl ether, diisopropyl ether, oxane, THF, ethylene glycol dimethyl ether and the like; and mixtures thereof.

After the reaction is completed, for example, the compound of the invention as desired can be obtained by treatments described in the following 1) or 2):

1) The reaction solution is poured into water, followed by extraction with an organic solvent, drying and concentration of the obtained organic layer, and chromatography of the residue.

2) The reaction solution is concentrated, followed by chromatography of the residue.

The product obtained by the treatment 1) or 2) can be purified by a treatment such as recrystallization or the like.

Production Process 3

The compound of the invention can be produced by reacting a compound represented by Chemical Formula 6:

[Chemical Formula 6]

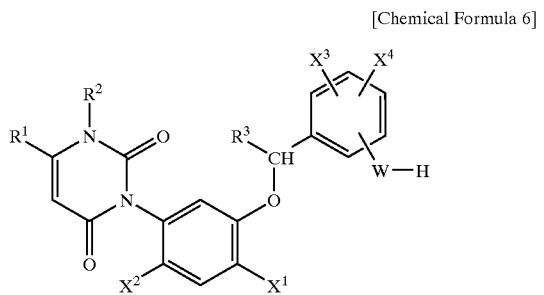

wherein $R^1$, $R^2$, $R^3$, W, $X^1$, $X^2$, $X^3$ and $X^4$ have the same meaning as above, with a compound represented by Chemical Formula 7:

[Chemical Formula 7]

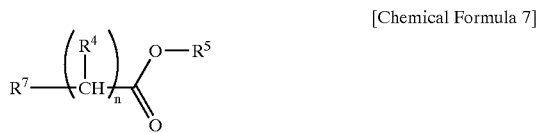

wherein $R^4$, $R^5$ and n have the same meaning as above and $R^7$ represents a leaving group such as chlorine, bromine, iodine, methanesulfonyloxy, p-toluenesulfonyloxy and the like, in the presence of a base.

Said reaction is usually carried out in a solvent; the range of the reaction temperature is 0 to 200° C. and the range of the reaction period is usually a moment to 72 hours.

The amount of the reagents used for the reaction may optionally be varied according to circumstances, while the theoretical amount of the compound represented by Chemical Formula 7 is 1 mole and the amount of the base is 1 mole, based on 1 mole of the uracil compound represented by Chemical Formula 6.

Usable base includes organic bases such as pyridine, quinoline, benzyldimethylamine, phenethyldimethylamine, N-methylmorpholine, 1,8-diazabicyclo[5.4.0]undec-7-ene, 1,5-diazabicyclo[4.3.0]non-5-ene, 1,4-bicyclo[2.2.2]octane, 4-dimethylaminopyridine, N,N-dimethylaniline, N,N-diethylaniline, triethylamine, tri-n-propylamine, triisopropylamine, tri-n-butylamine, diIsopropylethyalmine and the like; metal alkoxide such as sodium methoxide, sodium ethoxide potassium t-butoxide and the like, and inorganic bases such as lithium carbonate, sodium carbonate, potassium carbonate, calcium carbonate, barium carbonate, lithium hydrogen carbonate, sodium hydrogen carbonate, potassium hydrogen carbonate, calcium hydrogen carbonate, barium hydrogen carbonate, sodium hydride, potassium carbonate, lithium hydroxide, sodium hydroxide, potassium hydroxide, calcium hydroxide, barium hydroxide and the like.

The solvent includes, for example, aliphatic hydrocarbons such as n-hexane, n-heptane, ligroin, cyclohexane, petroleum ether and the like; aromatic hydrocarbons such as benzene, toluene, xylene and the like; halogenated aromatic hydrocarbons such as chlorobenzene, dichlorobenzene, benzotrifluolide and the like; ethers such as diethyl ether, diisopropyl ether, methyl t-butyl ether, dioxane, tetrahydrofuran, ethylene glycol dimethyl ether and the like; ketones such as acetone, 2-butanone, methyl isobutyl ketone and the like; esters such as ethyl formate, ethyl acetate, butyl acetate, diethyl carbonate and the like; nitro compounds such as nitromethane, nitrobenzene and the like; nitriles such as acetonitrile, isobutyronitrile and the like; acid amides such as N,N-dimethylformamide, N,N-dimethylacetamide and the like; sulfur compounds such as DMSO, sulfolane and the like; alcohols such as methanol, ethanol, ethylene glycol, isopropanol, t-butanol and the like; and mixtures thereof.

After the reaction is completed, the compound of the invention as desired can be obtained by treatments described in the following 1) or 2):

1) The reaction solution is poured into water, followed by extraction with an organic solvent, drying and concentration of the obtained organic layer.

2) The reaction solution is concentrated, or the reaction solution is filtered and the filtrate is concentrated.

The product obtained by the treatment 1) or 2) can be purified by a treatment such as chromatography, recrystallization or the like.

Production Process 4

The compound of the invention can be produced by reacting a compound represented by Chemical Formula 8:

[chemical Formula 8]

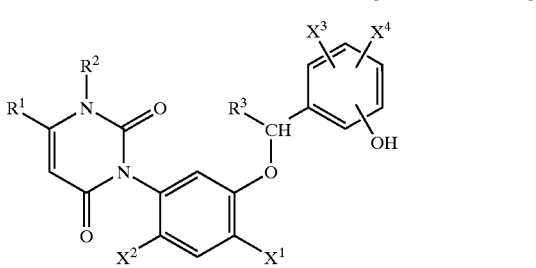

wherein $R^1$, $R^2$, $R^3$, $X^1$, $X^2$, $X^3$ and $X^4$ have the same meaning as above, with an alcohol compound represented by Chemical Formula 9:

[Chemical Formula 9]

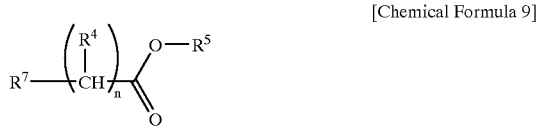

wherein $R^4$, $R^5$ and n have the same meaning as above, in the presence of a dehydrating agent.

The dehydrating agent includes, for example, a combination of a triarylphosphine such as triphenylphosphine and the like or a trialkylphosphine such as triethylphosphine and the like, and di(lower alkyl) azodicarboxylate such as diethyl azodicarboxylate, diisopropyl azodicarboxylate and the like.

Said reaction is usually carried out in a solvent; the range of the reaction temperature is −20 to 150° C., preferably 0 to 100° C., and the range of the reaction period is usually a moment to 48 hours.

The amount of the reagents used for the reaction is 1 to 3 moles, preferably 1 to 1.2 mole, for the alcohol compound represented by Chemical Formula 9; 1 to 3 moles, preferably 1 to 1.2 mole, for the triarylphosphine or trialkylphosphine; and 1 to 3 moles, preferably 1 to 1.2 mole, for the di(lower alkyl) azodicarboxylate, based on 1 mole of the uracil compound represented by Chemical Formula 8. The proportion of these reagents can optionally be varied according to circumstances.

The solvent used in the invention includes aliphatic hydrocarbons such as n-hexane, n-heptane, ligroin, cyclohexane, petroleum ether and the like; aromatic hydrocarbons such as benzene, toluene, xylene and the like; halogenated aromatic hydrocarbons such as chlorobenzene, dichlorobenzene, benzotrifluolide and the like; ethers such as diethyl ether, diisopropyl ether, dioxane, THF, ethylene glycol dimethyl ether and the like; and mixtures thereof.

After the reaction is completed, the compound of the invention as desired can be obtained by treatments described in the following 1) or 2):

1) The reaction solution is poured into water, followed by extraction with an organic solvent, drying and concentration of the obtained organic layer, and chromatography of the residue.

2) The reaction solution is concentrated, followed by chromatography of the residue.

The product obtained by the treatment 1) or 2) can be purified by a treatment such as recrystallization or the like.

Production Process 5

The compound of the invention can be produced from a carboxylic acid compound represented by Chemical Formula 10:

[Chemical Formula 10]

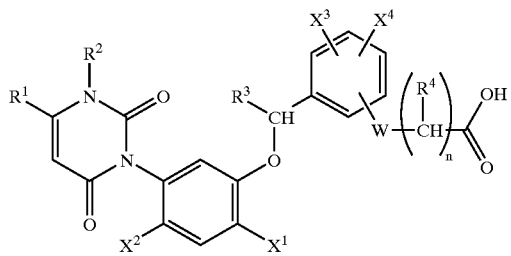

wherein $R^1$, $R^2$, $R^3$, $R^4$, W, $X^1$, $X^2$, $X^3$, $X^4$ and n have the same meaning as above, with an alcohol compound represented by Chemical Formula 11:

$R^5$—OH  [Chemical Formula 11]

wherein $R^5$ has the same meaning as above.

The above reaction is carried out by a method in which the carboxylic acid compound represented by Chemical Formula 10 is converted to an acid chloride by the reaction with a chlorinating agent (hereinafter, referred to as <Step 1-1>) and then reacted with an alcohol compound represented by Chemical Formula 11 in the presence of a base (hereinafter, referred to as <Step 1-2>).

<Step 1-1> is carried out without solvent or in a solvent; the range of the reaction temperature is 0 to 150° C. and the range of the reaction period is usually a moment to 24 hours.

The amount of the reagents used for the reaction may optionally be varied according to circumstances, while the theoretical amount of the chlorinating agent is 1 mole based on 1 mole of the compound represented by Chemical Formula 10.

Usable chlorinating agent includes, for example, thionyl chloride, sulfuryl chloride, phosgene, oxalyl chloride, phosphor trichloride, phosphor pentachloride, phosphor oxychloride and the like.

The solvent includes, for example, aliphatic hydrocarbons such as n-hexane, n-heptane, nonane, decane, ligroin, cyclohexane, petroleum ether and the like; aromatic hydrocarbons such as benzene, toluene, xylene, mesitylene and the like; halogenated aliphatic hydrocarbons such as methylene chloride, chloroform, carbon tetrachloride, 1,2-dichloroethane, 1,2,3-trichloropropane and the like; halogenated aromatic hydrocarbons such as monochlorobenzene, dichlorobenzene, benzotrifluolide and the like; ethers such as diethyl ether, diisopropyl ether, methyl t-butyl ether, 1,4-dioxane, tetrahydrofuran, ethylene glycol dimethyl ether and the like; and mixtures thereof.

After the reaction is completed, the reaction solution is, for example, concentrated and the residue of concentration is used in <Step 1-2> as it is.

<Step 1-2> is carried out without solvent or in a solvent; the range of the reaction temperature is −20 to 100° C. and the range of the reaction period is usually a moment to 24 hours.

The amount of the reagents used for the reaction may optionally be varied according to circumstances, while the theoretical amount of the alcohol compound represented by Chemical Formula 11 and the base is 1 mole and 1 mole, respectively, based on 1 mole of the compound represented by Chemical Formula 10.

Usable base includes inorganic bases such as lithium hydrogen carbonate, sodium hydrogen carbonate, potassium hydrogen carbonate, lithium carbonate, sodium carbonate, potassium carbonate and the like; nitrogen-containing aromatic compounds such as pyridine, quinoline, 4-dimethylaminopyridine, 2-picoline, 3-picoline, 4-picoline, 2,3-lutidine, 2,4-lutidine, 2,5-lutidine, 2,6-lutidine, 3,4-lutidine, 3,5-lutidine, 3-chloropyridine, 2-ethyl-3-methylpyridine, 5-ethyl-2-mwthylpyridine and the like; tertiary amines such as triethylamine, diusopropylethylamine, tri-n-propylamine, tri-n-butylamine, benzyldimethylamine, phenethyldimethylamine, N-methylmorpholine, 1,8-diazabicyclo[5.4.0]undec-7-ene, 1,5-diazabicyclo[4.3.0]non-5-ene, 1,4-bicyclo[2.2.2]octane and the like.

The solvent includes, for example, aliphatic hydrocarbons such as n-hexane, n-heptane, nonane, decane, ligroin, cyclohexane, petroleum ether and the like; aromatic hydrocarbons such as benzene, toluene, xylene, mesitylene and the like; halogenated aliphatic hydrocarbons such as methylene chloride, chloroform, carbon tetrachloride, 1,2-dichloroethane, 1,2,3-trichloropropane and the like; halogenated aromatic hydrocarbons such as monochlorobenzene, dichlorobenzene, benzotrifluolide and the like; ethers such as diethyl ether, diisopropyl ether, methyl t-butyl ether, 1,4-dioxane, tetrahydrofuran, ethylene glycol dimethyl ether and the like; and mixtures thereof.

After the reaction is completed, the compound of the invention as desired can be obtained by treatments described in the following 1) or 2):

1) The reaction solution is poured into water, followed by extraction with an organic solvent, drying and concentration of the obtained organic layer.

2) The reaction solution is concentrated, or the reaction solution is filtered and the filtrate is concentrated.

The product obtained by the treatment 1) or 2) can be purified by a treatment such as chromatography, recrystallization or the like.

In addition to the above-described <Step 1-1>and <Step 1-2>, Production Process 5 with the carboxylic acid compound represented by Chemical Formula 10 and the alcohol compound represented by Chemical Formula 11 can be carried out in the presence of a condensing agent such as carbonyldiumidazol, dicyclohexylcarbodiimide or the like; in the presence of an acid catalyst; or according to other known methods.

Production Process 6

The compound of the invention wherein $R^5$ is a substituent other than methyl or ethyl can be produced by reacting a compound represented by Chemical Formula 12:

[Chemical Formula 12]

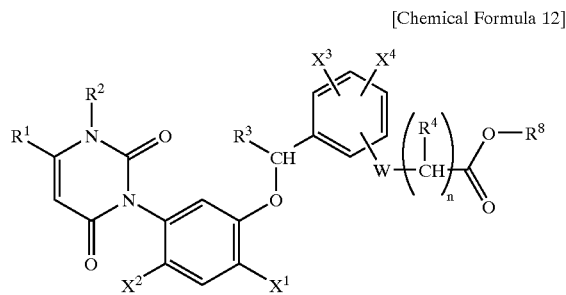

wherein $R^1$, $R^2$, $R^3$, $R^4$, W, $X^1$, $X^2$, $X^3$, $X^4$ and n have the same meaning as above, and $R^8$ represents methyl or ethyl, with an alcohol compound represented by Chemical Formula 13:

  [Chemical Formula 13]

wherein $R^{12}$ represents $C_3$- to $C_6$-alkyl, $C_1$ to $C_6$-haloalky, $C_3$- to $C_6$-alkenyl, $C_3$- to $C_6$-haloalkenyl, $C_3$- to $C_6$-alkynyl or $C_3$- to $C_6$-haloalkynyl, in the presence of a catalyst.

Said reaction is usually carried out without solvent or in a solvent; the range of the reaction temperature is 0 to 200° C. and the range of the reaction period is usually a moment to 24 hours.

The amount of the reagents used for the reaction may optionally be varied according to circumstances, with the excess amount of the compound represented by Chemical Formula 13 being preferred, while the theoretical amount of the compound represented by Chemical Formula 13 is 1 mole based on 1 mole of the compound represented by Chemical Formula 12.

Usable catalyst includes alkali metal alkoxides such as potassium alkoxide, sodium alkoxide and the like; inorganic acids such as phosphoric acid, sulfuric acid and the like; and organic acids such as p-toluenesulfonic acid and the like.

In addition, the reaction can be promoted by removing methanol or ethanol formed according to the progress of the reaction.

The solvent includes, for example, aliphatic hydrocarbons such as n-hexane, n-heptane, nonane, decane, ligroin, cyclohexane, petroleum ether and the like; aromatic hydrocarbons such as benzene, toluene, xylene, mesitylene and the like; halogenated aliphatic hydrocarbons such as 1,2,3-trichloropropane and the like; halogenated aromatic hydrocarbons such as monochlorobenzene, dichlorobenzene, benzotrifluolide and the like; ethers such as ethylene glycol dimethyl ether and the like; and mixtures thereof. In the case where the amount of the alcohol compound represented by Chemical Formula 13 is excess, the solvent is not necessary.

After the reaction is completed, the compound of the invention as desired can be obtained by treatments described in the following 1) or 2):

1) The reaction solution is poured into water, followed by extraction with an organic solvent, drying and concentration of the obtained organic layer.

2) The reaction solution is concentrated or the reaction solution is filtered and the filtrate is concentrated.

The product obtained by the treatment 1) or 2) can be purified by a treatment such as chromatography, recrystallization or the like.

The uracil compound represented by Chemical Formula 3 is a known compound in JP-A-63-41466 and the like.

The compounds represented by Chemical Formula 7, the alcohol compounds represented by Chemical formula 9, the alcohol compounds represented by Chemical Formula 11 and the alcohol compounds represented by Chemical formula 13 are commercially available or can be obtained by producing according to known processes.

The carboxylic acid compounds represented by Chemical Formula 10 can be produced by acid hydrolysis of the compounds of the invention represented by Chemical Formula 2.

The compounds represented by Chemical formula 12 can be produced according to the methods shown in Production Processes 1 to 5.

The compounds represented by Chemical Formula 4 and the compounds represented by Chemical Formula 5 can be produced specifically, for example, by the processes described in (Reference Production Process 1) and (Reference Production Process 2) shown below.

Reference Production Process 1

The compounds represented by Chemical Formula 4 and the compounds represented by Chemical Formula 5 can be produced according to the following scheme:

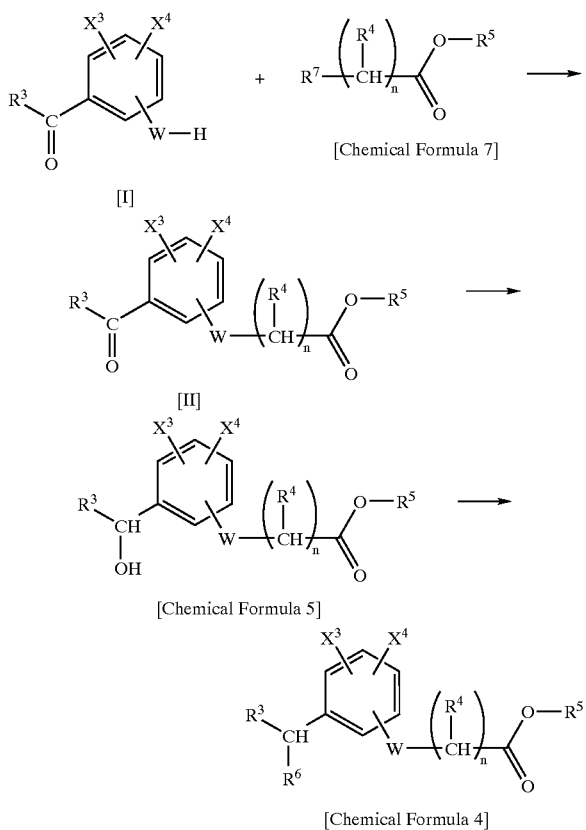

wherein $R^3$, $R^4$, $R^5$, $R^6$, $R^7$, W, $X^3$, $X^4$ and n have the same meaning as above.

<Step 1>

A step for producing the compound [II] from the compound [T]:

The compound [II] can be produced by reacting the compound [I] with the compound represented by Chemical Formula 7, in the presence of a base.

Said reaction is usually carried out in a solvent; the range of the reaction temperature is usually 0 to 200° C. and the range of the reaction period is usually a moment to 72 hours.

The amount of the reagents used for the reaction can optionally be varied according to circumstances, while the theoretical amount of the compound represented by Chemical Formula 7 is 1 mole and the amount of the base is 1 mole, based on 1 mole of the compound [I].

Usable base includes organic bases such as pyridine, quinoline, benzyldimethylamine, phenethyldimethylamine, N-methylmorpholine, 1,8-diazabicyclo[5.4.0]undec-7-ene, 1,5-diazabicyclo[4.3.0]non-5-ene, 1,4-bicyclo[2.2.2]octane, 4-dimethylaminopyridine, N,N-dimethylaniline, N,N-diethylaniline, triethylamine, tri-n-propylamine, triisopropylamine, tri-n-butylamine, diisopropylethyamine and the like; metal alkoxide such as sodium methoxide, sodium ethoxide, potassium t-butoxide and the like; and inorganic bases such as lithium carbonate, sodium carbonate, potassium carbonate, calcium carbonate, barium carbonate, lithium hydrogen carbonate, sodium hydrogen carbonate, potassium hydrogen carbonate, calcium hydrogen carbonate, barium hydrogen carbonate, sodium hydride, potassium carbonate, lithium hydroxide, sodium hydroxide, potassium hydroxide, calcium hydroxide, barium hydroxide and the like.

The solvent includes, for example, aliphatic hydrocarbons such as n-hexane, n-heptane, ligroin, cyclohexane, petroleum ether and the like; aromatic hydrocarbons such as benzene, toluene, xylene and the like; halogenated aromatic hydrocarbons such as chlorobenzene, dichlorobenzene, benzotrifluolide and the like; ethers such as diethyl ether, diisopropyl ether, methyl t-butyl ether, dioxane, tetrahydrofuran, ethylene glycol dimethyl ether and the like; ketones such as acetone, 2-butanone, methyl isobutyl ketone and the like; esters such as ethyl formate, ethyl acetate, butyl acetate, diethyl carbonate and the like; nitro compounds such as nitromethane, nitrobenzene and the like; nitriles such as acetonitrile, isobutyronitrile and the like; acid amides such as N,N-dimethylformamide, N,N-dimethylacetamide and the like; sulfur compounds such as dimethylsulfoxide, sulfolane and the like; alcohols such as methanol, ethanol, ethylene glycol, isopropanol, t-butanol and the like; and mixtures thereof.

After the reaction is completed, the compound of the invention as desired can be obtained by treatments described in the following 1) or 2):

1) The reaction solution is poured into water, followed by extraction with an organic solvent, drying and concentration of the obtained organic layer.

2) The reaction solution is concentrated or the reaction solution is filtered and the filtrate is concentrated.

The product obtained by the treatment 1) or 2) can be purified by a treatment such as chromatography, recrystallization or the like.

<Step 2>

A step for producing the compound represented by Chemical Formula 5 from the compound [II]:

The compound represented by Chemical Formula 5 can be produced, for example, by reducing the compound [II] with sodium borohydride in methanol, or by subjecting the compound [II] to catalytic hydrogenation over palladium on carbon as the catalyst. (See J. Heterocyclic Chem., 24, 495 (1987) and J. Org. Chem., 25, 137 (1960).)

<Step 3a>

A step for producing the compound represented by Chemical Formula 4 wherein $R^6$ is chlorine, bromine or iodine from the compound represented by Chemical Formula 5:

The compound represented by Chemical Formula 4 wherein $R^6$ is chlorine or bromine can be produced by brominating the compound represented by Chemical Formula 5 with phosphor tribromide, chlorinating with thionyl chloride or otherwise. The compound represented by Chemical Formula 4 wherein $R^6$ is iodine can be produced by reacting the compound represented by Chemical Formula 4 wherein $R^6$ is bromine or chlorine with sodium iodide or the like. (See J. Amer. Chem. Soc., 74, 3688 (1952), J. Amer. Chem. Soc., 72, 1655 (1950), Synlett., 7, 489 (1993) and others.)

<Step 3b>

A step for producing the compound represented by Chemical Formula 4 wherein $R^6$ is methanesulfonyloxy or p-toluenesulfonyloxy from the compound represented by Chemical Formula 5:

The compound represented by Chemical Formula 4 wherein $R^6$ is methanesulfonyloxy or p-toluenesulfonyloxy can be produced by reacting the compound represented by Chemical Formula 5 with methanesulfonyl chloride or p-toluenesulfonyl chloride, or otherwise. (See J. Org. Chem., 39, 1036 (1974), Synthesis, 665 (1974) and others)

Reference Production Process 1-2

The compounds represented by Chemical Formula 5 can also be produced according to the following scheme:

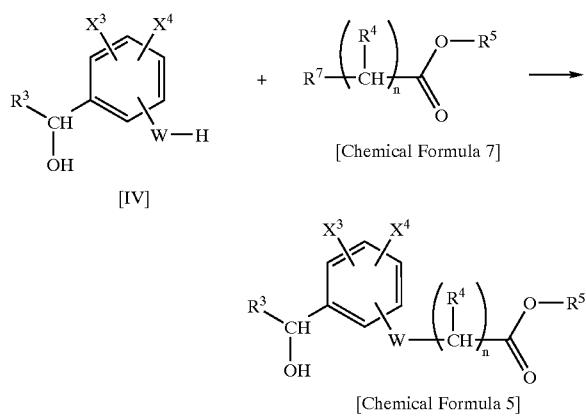

[Chemical Formula 7]

[Chemical Formula 5]

wherein $R^3$, $R^4$, $R^5$, $R^7$, W, $X^3$, $X^4$ and n have the same meaning as above.

The compound represented by Chemical Formula 5 can be produced by reacting the compound [IV] with the compound represented by Chemical Formula 7 in the presence of a base. (See Reference Production Process 1, <Step 1>.)

Reference Production Process 2

The compound represented by Chemical Formula 4 wherein $R^6$ is chlorine, bromine or iodine can also be produced according to the following scheme:

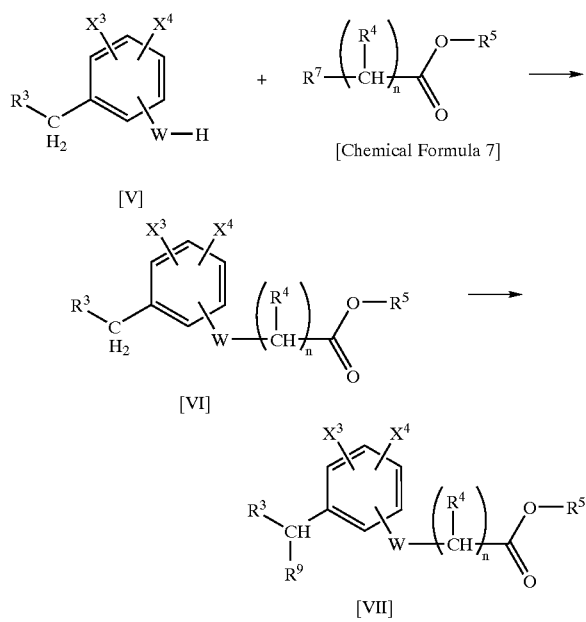

[Chemical Formula 7]

[VI]

[VII]

wherein $R^3$, $R^4$, $R^5$, $R^7$, W, $X^3$, $X^4$ and n have the same meaning as above, and $R^7$ represents chlorine, bromine or iodine.

<Step 1>

A step for producing the compound [VI] from the compound [V]:

The compound [VI] can be produced by reacting the compound [VI] with the compound represented by Chemical Formula 7 in the presence of a base.

Said reaction is usually carried out in a solvent; the range of the reaction temperature is usually 0 to 200° C. and the range of the reaction period is usually a moment to 72 hours.

The amount of the reagents used for the reaction can optionally be varied according to circumstances, while the theoretical amount of the compound represented by Chemical Formula 7 is 1 mole and the amount of the base is 1 mole, based on 1 mole of the compound [V].

Usable base includes organic bases such as pyridine, quinoline, benzyldimethylamine, phenethyldimethylamine, N-methylmorpholine, 1,8-diazabicyclo[5.4.0]undec-7-ene, 1,5-diazabicyclo[4.3.0]non-5-ene, 1,4-diazabicyclo[2.2.2]octane, 4-dimethylaminopyridine, N,N-dimethylaniline, N,N-diethylaniline, triethylamine, tri-n-propylamine, triisopropylamine, tri-n-butylamine, diisopropylethyalmine and the like; metal alkoxide such as sodium methoxide, sodium ethoxide, potassium t-butoxide and the like; and inorganic bases such as lithium carbonate, sodium carbonate, potassium carbonate, calcium carbonate, barium carbonate, lithium hydrogen carbonate, sodium hydrogen carbonate, potassium hydrogen carbonate, calcium hydrogen carbonate, barium hydrogen carbonate, sodium hydride, potassium carbonate, lithium hydroxide, sodium hydroxide, potassium hydroxide, calcium hydroxide, barium hydroxide and the like.

The solvent includes, for example, aliphatic hydrocarbons such as n-hexane, n-heptane, ligroin, cyclohexane, petroleum ether and the like; aromatic hydrocarbons such as benzene, toluene, xylene and the like; halogenated aromatic hydrocarbons such as chlorobenzene, dichlorobenzene, benzotrifluolide and the like; ethers such as diethyl ether, diisopropyl ether, methyl t-butyl ether, dioxane, tetrahydrofuran, ethylene glycol dimethyl ether and the like; ketones such as acetone, 2-butanone, methyl isobutyl ketone and the like; esters such as ethyl formate, ethyl acetate, butyl acetate, diethyl carbonate and the like; nitro compounds such as nitromethane, nitrobenzene and the like; nitrites such as acetonitrile, isobutyronitrile and the like; acid amides such as N,N-dimethylformamide, N,N-dimethylacetamide and the like; sulfur compounds such as dimethylsulfoxide, sulfolane and the like; alcohols such as methanol, ethanol, ethylene glycol, isopropanol, t-butanol and the like; and mixtures thereof.

After the reaction is completed, the compound of the invention as desired can be obtained by treatments described in the following 1) or 2):

1) The reaction solution is poured into water, followed by extraction with an organic solvent, drying and concentration of the obtained organic layer.
2) The reaction solution is concentrated or the reaction solution is filtered and the filtrate is concentrated.

The product obtained by the treatment 1) or 2) can be purified by a treatment such as chromatography, recrystallization or the like.

<Step 2>

A step for producing the compound [VII] from the compound [VI]:

The compound [VII] wherein $R^9$ is chlorine or bromine can be produced by brominating the compound [VI] with N-bromosuccinimide or bromine, or chlorinating the same with chlorine.

The compound [VII] wherein $R^9$ is iodine can be produced by reacting the compound [VII] wherein $R^9$ is chlorine or bromine with sodium iodide. (See J. Chem. Soc., 1030 (1951), Ber. Dtsch. Chem. Ges., 43, 1528 (1910) and others.)

The compounds represented by Chemical Formula 6 can be produced specifically, for example, by processes described in (Reference Production Process 3) shown below:

Reference Production Process 3

The compounds represented by Chemical Formula 6 can be produced according to the following scheme:

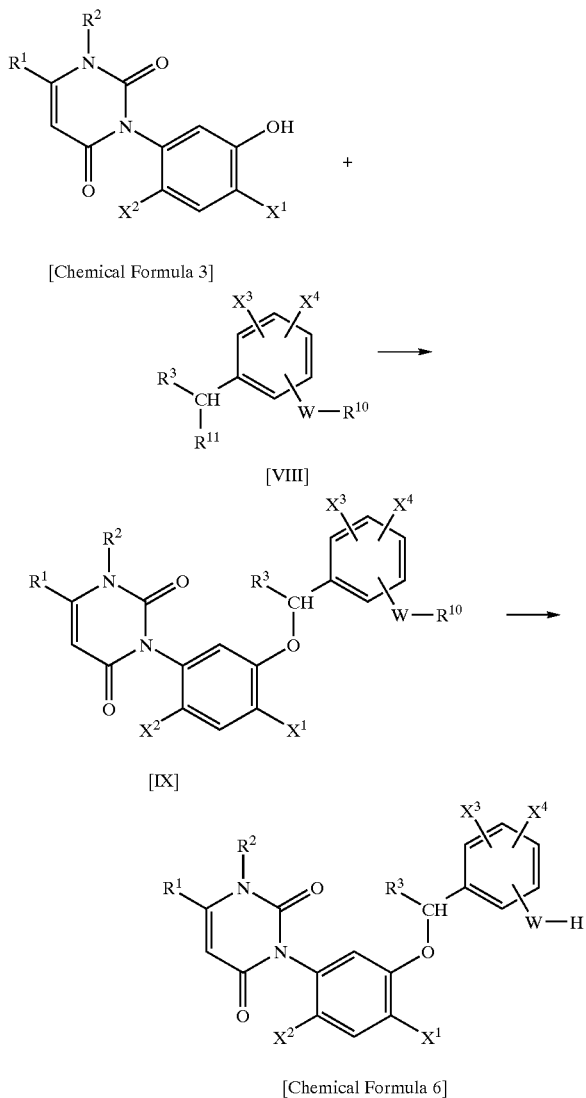

wherein $R^1$, $R^2$, $R^3$, W, $X^1$, $X^2$, $X^3$ and $X^4$ have the same meaning as above, and $R^{10}$ represents a protecting group such as t-butyldimethylsilyl, t-butyl, benzyl, methoxymethyl, acetyl, methoxycarbonyl, ethoxycarbonyl or the like, and $R^{11}$ represents a leaving group such as chlorine, bromine, iodine, methanesulfonyloxy, p-toluenesulfonyloxy or the like.

<Step 1>

A step for producing the compound [IX] from the compound represented by Chemical Formula 3:

The compound [IX] can be produced by reacting the compound represented by Chemical Formula 3 with the compound [VIII] in the presence of a base, (See Production Process 1.)

<Step 2>

A step for producing the compound represented by Chemical Formula 6 from the compound [IX]:

The compound represented by Chemical Formula 6 can be produced by deprotecting the compound [IX] with boron tribromide, HBr/acetic acid, concentrated hydrochloric acid or concentrated sulfuric acid, in methylene chloride, ethyl acetate or water, according to the method described in Protective Groups in Organic Synthesis (A Wiley-Interscience Publication).

Reference Production Process 3-1

The compound [IX] can also be produced according to the following scheme:

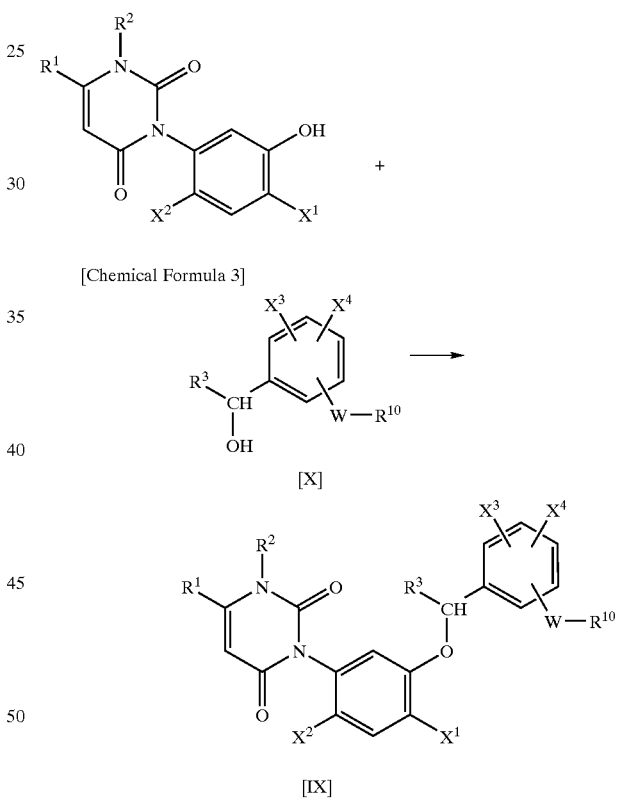

wherein $R^1$, $R^2$, $R^3$, $R^{10}$, W, $X^1$, $X^2$, $X^3$ and $X^4$ have the same meaning as above.

The compound [IX] can be produced by reacting the compound represented by Chemical Formula 3 with the compound [X]. (See Production Process 2.)

Reference Production Process 3-2

The compound [VIII] and the compound [X] can be produced according to the following scheme:

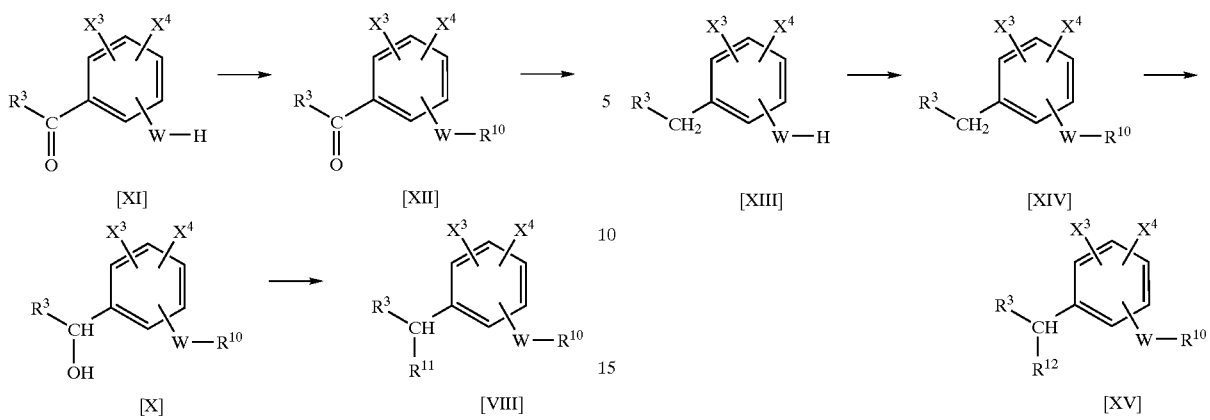

wherein $R^1$, $R^{10}$, $R^{11}$, W, $X^3$ and $X^4$ have the same meaning as above.

<Step 1>

A step for producing the compound [XII] from the compound [XI]:

The compound [XII] can be produced by reacting the compound [XI] with t-butyldimethylsilyl chloride, isobutene, methoxymethyl chloride, acetyl chloride, methyl chlorocarbonate, ethyl chloroformate or the like. (See Protective Groups in Organic Synthesis (A Wiley-Interscience Publication).)

<Step 2>

A step for producing the compound [X] from the compound [XII]:

The compound [X] can be produced by reducing the compound [XII] with sodium borohydride in methanol, or by subjecting the compound [XII] to catalytic hydrogenation over palladium on carbon as the catalyst. (See J. Heterocyclic Chem., 24, 495 (1987) and J. Org. Chem., 25, 137 (1960).)

<Step 3a>

A step for producing the compound [VIII] wherein $R^{11}$ is chlorine, bromine or iodine from the compound [X]:

The compound [VIII] wherein $R^{11}$ is chlorine or bromine can be produced by brominating the compound [X] with phosphor tribromide, chlorinating with thionyl chloride or otherwise. The compound [VIII] wherein $R^{11}$ is iodine can be produced by reacting the compound [VIII] wherein $R^{11}$ is bromine or chlorine with sodium iodide or the like. (See J. Amer. Chem. Soc., 74, 3688 (1952), J. Amer. Chem. Soc., 72, 1655 (1950), Synlett., 7, 489 (1993) and others.)

<Step 3b>

A step for producing the compound [VIII] wherein $R^{10}$ is methanesulfonyloxy or p-toluenesulfonyloxy from the compound [X]:

The compound [VIII] wherein $R^{10}$ is methanesulfonyloxy or p-toluenesulfonyloxy can be produced by reacting the compound [X] with methanesulfonyl chloride or p-toluenesulfonyl chloride or otherwise. (See J. Org. Chem., 39, 1036 (1974), Synthesis, 665 (1974) and others).

Reference Production Process 3-3

The compound [VIII] wherein $R^{11}$ is chlorine, bromine or iodine can also be produced according to the following scheme:

wherein $R^3$, $R^{10}$, W, $X^3$ and $X^4$ have the same meaning as above, and $R^{12}$ represents chlorine, bromine or iodine.

<Step 1>

A step for producing the compound [XIV] from the compound [XIII]:

The compound [XIV] can be produced by reacting the compound [XIII] with t-butyldimethylsilyl chloride, isobutene, methoxymethyl chloride, acetyl chloride, methyl chlorocarbonate, ethyl chloroformate or the like. (See Protective Groups in Organic Synthesis (A Wiley-Interscience Publication).)

<Step 2>

A step for producing the compound [XV] from the compound [XIV]:

The compound [XV] wherein $R^{12}$ is chlorine or bromine can be produced by brominating the compound [XIV] with N-bromosuccinimide or bromine or the like, or chlorinating the same with chlorine or the like.

The compound [XV] wherein $R^{12}$ is iodine can be produced by reacting the compound [XV] wherein $R^{12}$ is chlorine or bromine with sodium iodide. (See J. Chem. Soc., 1030 (1951), Ber. Dtsch. Chem. Ges., 43, 1528 (1910) and others.)

The compound [I], the compound [IV], the compounds [V], the compound [XI] and the compound [XIII] are commercially available or can be produced according to known processes.

The compounds of the invention have excellent herbicidal effect and some of them can exhibit excellent selectivity between crops and weeds. In other words, the compound of the invention has herbicidal effect against various weeds which may cause some trouble in the foliar treatment and the soil treatment on upland fields, such as listed below.

Onagraceae weeds:
large-flowered eveningprimrose (*Oenothera erythrosepala*), common eveningprimrose (*Oenothera biennis*), cutleaf eveningprimrose (*Oenothera laciniata*)

Ranunculaceae weeds:
roughseed buttercup (*Ranunculus muricatus*), hairy buttercup (*Ranunculus sardous*)

Polygonaceous weeds:
wild buchwheat (*Polygonum convolvulus*), pale smartweed (*Polygonum lapathifolium*), Pensylvania smartweed (*Polygonum pensylvanicum*), ladysthumb (*Polygonum persicaria*), Japanese knotweed (*Polygonum cuspidatum*), prostrate knotweed (*Polygonum aviculare*), curly dock (*Rumex crispus*), broadleaf dock (*Rumex obtusifolius*), red sorrel (*Rumex acetosella*)

Portulacaceous weeds:
common purslane (*Portulaca oleracea*)
Caryophyllaceous weeds:
common chickweed (*Stellaria media*), sticky chickweed (*Cerastium glomeratum*)
Chenopodiaceous weeds:
common lambsquarters (*Chenopodium album*), kochia (*Kochia scoparia*)
Amaranthaceous weeds:
redroot pigweed (*Amaranthus retroflexus*), smooth pigweed (*Amaranthus hybridus*), palmer amaranth (*Amaranthus palmeri*), tall waterhemp (*Amaranthus tuberculatus*), common waterhemp (*Amaranthus rudis*)
Cruciferous weeds:
wild radish (*Raphanus raphanistrum*), wild mustard (*Sinapis arvensis*), shepherdspurse (*Capsella bursa-pastoris*), Virginia pepperweed (*Lepidium virginicum*)
Leguminous weeds:
hemp sesbania (*Sesbania exaltata*), sicklepod (*Cassia obtusifolia*), Florida beggarweed (*Desmodium tortuosum*), white clover (*Trifolium repens*), common vetch (*Vicia sativa*), black medick (*Medicago lupulina*)
Papaveraceous weeds:
common poppy (*Papaver rhoeas*)
Malvaceous weeds:
velvetleaf (*Abutilon theophrasti*), prickly sida (*Sida spinosa*), venice mallow (*Hibiscus trionum*)
Violaceous weeds:
field pansy (*Viola arvensis*), wild pansy (*Viola tricolor*)
Rubiaceous weeds:
catchweed bedstraw (*cleavers*) (*Galium aparine*)
Convolvulaceous weeds:
ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa*), field bindweed (*Convolvulus arvensis*), hedge bindweed (*Calystegia sepium*)
Labiate weeds:
red deadnettle (*Lamium purpureum*), henbit (*Lamium amplexicaule*)
Solanaceous weeds:
jimsonweed (*Datura stramonium*), black nightshade (*Solanum nigrum*), horsenettle (*Solanum carolinense*)
Scrophulariaceous weeds:
birdseye speedwell (*Veronica persica*), corn speedwell (*Veronica arvensis*), ivyleaf speedwell (*Veronica hederifolia*)
Composite weeds:
heartleaf cocklebur (*Xanthium strumarium*), common sunflower (*Helianthus annuus*), wild camomille (*Matricaria chamomilla*), scentless chamomile (*Matricaria perforata* or *inodora*), pineappleweed (*Matricaria matricarioides*), corn marigold (*Chrysanthemum segetum*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*), late goldenrod (*Solidago gigantea*), common dandelion (*Taraxacum officinale*), common groundsel (*Senecio vulgaris*), hairy galinsoga (*Galinsoga ciliata*)
Boraginaceous weeds:
forget-me-not (*Myosotis scorpioides*), field forget-me-not (*Myosotis arvensis*)

Asclepiadaceous weeds:
common milkweed (*Asclepias syriaca*)
Euphorbiaceous weeds:
sun spurge (*Euphorbia helioscopia*), spotted spurge (*Euphorbia maculata*)
Geraniaceae weeds:
carolina geranium (*Geranium carolinianum*)
Oxalidaceae weeds:
yellow flowersorrel (*Oxalis corymbosa*)
Cucurbitaceae weeds:
burcucumber (*Sicyos angulatus*)
Graminaceous weeds:
barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oat (*Avena fatua*), silky bentgrass (*Apera spica-venti*), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texanum*), shattercane (*Sorghum vulgare*), woolly cupgrass (*Eriochloa villosa*), water foxtail (*Alopecurus geniculatus*)
Commelinaceous weeds:
common dayflower (*Commelina communis*), tropical spiderwort (*Commelina benghalensis*)
Equisetaceous weeds:
field horsetail (*Equisetum arvense*)
Cyperaceous weeds:
rice flatsedge (*Cyperus iria*), purple nutsedge (*Cyperus rotundus*), yellow nutsedge (*Cyperus esculentus*)

Furthermore, some of the compounds of the invention exhibit no significant phytotoxicity on the main crops including corn (*Zea mays*), wheat (*Triticum aestivum*), barley (*Hordeum vulgare*), rye (*Secale cereale*), oat (*Avena sativa*), rice (*Oryza sativa*), grain sorghum (*Sorghum bicolor*), soybean (*Glycine max*), cotton (*Gossypium* spp.), sugar beet (*Beta vulgaris*), peanut (*Arachis hypogaea*), common sunflower (*Helianthus annuus*), and rape (*Brassica napus*); and horticultural crops such as flowers, ornamental plants, and vegetable crops. The compounds of the invention can attain effective control of various weeds, which may cause some trouble in the no-tillage cultivation of crops such as soybean, corn and wheat.

The compounds of the invention also have herbicidal effect against various weeds, which may cause some trouble, in flooding treatment of paddy fields, such as listed below.
Graminaceous weeds:
barnyardgrass (*Echinochloa oryzoides*)
Scrophulariaceous weeds:
common false pimpernel (*Lindernia procumbens*), low false pimpernel (*Lindernia dubia* var. major)
Lythraceae weeds:
Indian toothcup (*Rotala indica*), redstem (*Ammannia multiflora*), valley redstem (*Ammannia coccinea*)
Elatinaceae weeds:
waterwort (*Elatine triandra*)
Cyperaceous weeds: smallflower umbrella sedge (*Cyperus difformis*), hardstem bulrush (*Scirpus juncoides* subsp. *hotarui*), Japanese bulrush (*Scirpus juncoides* subsp. *juncoides*), needle spikerush (*Eleocharis acicularis*), water nutsedge (*Cyperus serotinus*), water chestnut (*Eleocharis kuroguwai*)

Pontederiaceae weeds:
Monochoria (*Monochoria vaginalis*)
Alismataceae weeds:
arrowhead (*Sagittaria pygmaea*), arrowhead (*Sagittaria trifolia*), waterplantain (*Alisma canaliculatum*)
Potamogetonaceae weeds:
roundleaf pondweed (*Potamogeton distincutus*)
Umbelliferae weeds:
watercelery sp. (*Oenanthe javanica*)

Furthermore, some of the compounds of the invention exhibit no significant phytotoxicity on transplanted paddy rice.

The compounds of the invention can also be used to control a wide variety of weeds which are growing or will grow in non-cultivated lands in which weed controlling is necessitated such as a levee, riverbed, roadside, railroad, green field area of a park, ground, parking area, airport, industrial place (ex. factory, storage equipment), fallow field, idle land of an urban area; wood lot, grasslands, lawns, forests, and the like. The compounds of the invention also have herbicidal effect against various aquatic weeds, such as water hyacinth (*Eichhornia crassipes*), which are growing or will grow at rivers, canals, waterways reservoirs and the like.

The compound of the inventions has the similar property of the herbicidal compounds described in WO 95/34659. In the case where crops with tolerance imparted by introducing a herbicide tolerance gene, described in the description of the file, or the like are cultivated, the compound of the invention can be used at larger dosages than those used when ordinary crops without tolerance are cultivated, which makes it possible to control other unfavorable weeds more effectively.

When the compound of the invention are used as the active ingredients of herbicides, they may be suitably mixed with solid or liquid carriers or diluents, surfactants, and other auxiliary agents to give emulsifiable concentrates, wettable powders, flowables, granules, concentrated emulsions, water-dispersible granules, or other formulations.

These formulations may contain any of the compounds of the invention as an active ingredient at an amount of about 0.001 to 80% by weight, preferably about 0.005 to 70% by weight, based on the total weight of the formulation.

Solid carriers for use in the present invention include, fine powders of mineral matters such as kaolin clay, attapulgite clay, bentonite, acid clay, pyrophyllite, talc, diatomaceous earth, calcite and the like; fine powders of organic substances such as walnut shell powder and the like; fine powders of water-soluble organic substances such as urea and the like; fine powders of inorganic salts such as ammonium sulfate and the like; and fine powders such as synthetic hydrated silica. Liquid carriers for use in the present invention include, aromatic hydrocarbons such as methylnaphthalene, phenyl xylylethane, alkylbenzene (e.g., xylene) and the like; alcohols such as isopropanol, ethylene glycol, 2-ethoxyethanol and the like; esters such as phthalic acid dialkyl esters and the like; ketones such as acetone, cyclohexanone isophorone and the like; mineral oils such as machine oil and the like; vegetable oils such as soybean oil and cotton seed oil and the like; dimethyl sulfoxide, N,N-dimethylformamide, acetonitrile, N-methylpyrrolidone, water and the like.

The surfactants used for emulsification, dispersing, or spreading include surfactants of the anionic type such as alkylsulfate salts, alkylsulfonic acid salts, alkylarylsulfonic acid salts, dialkylsulfosuccinate salts, phosphates of polyoxyethylene alkyl aryl ethers and the like; surfactants of the nonionic type such as polyoxyethylene alkyl ethers, polyoxyethylene alkyl aryl ethers, polyoxyethylene polyoxypropylene block copolymers, sorbitan fatty acid esters, polyoxyethylene sorbitan fatty acid esters and the like; and the like.

Other auxiliary agents utilized in the present invention include lignin sulfonete acid salts, alginic acid salts, polyvinyl alcohol, gum arabic, CMC (carboxymethylcellulose), and PAP (isopropyl acid phosphate) and the like.

The compounds of the invention are usually formulated and used for soil, foliar, or flooding treatment at pre- or post-emergence of weeds. The soil treatment may include soil surface treatment, soil incorporation and the like. The foliar treatment may include application over the plants and directed application in which a chemical is applied only to weeds so as to keep it off the crop plants.

The compounds of the invention may often exhibit the enhancement of herbicidal effect when used in admixture with other herbicides. They can also be used in admixture with insecticides, acaricides, nematocides, fungicides, bactericides, plant growth regulators, fertilizers, soil conditioners and the like.

The compounds may, for example, be used in admixture with the following herbicides. atrazine, cyanazine, dimethametryn, metribuzin, prometryn, simazine, simetryn, chlorotoluron, diuron, fluometuron, isoproturon, linuron, methabenzthiazuron, propanil, bentazone, bromoxynil, ioxynil, pyridate, butamifos, dithiopyr, ethalfluralin, pendimethalin, thiazopyr, trifluralin, acetochlor, alachlor, butachlor, diethatyl-ethyl, dimethenamid, fluthiamide, mefenacet, metolachlor, pretilachlor, propachlor, cinmethylin, acifluorfen, acifluorfen-sodium, benzfendizone, bifenox, butafenacil, chlomethoxynil, fomesafen, lactofen, oxadiazon, oxadiargyl, oxyfluorfen, carfentrazone-ethyl, fluazolate, flumiclorac-pentyl, flumioxazine, fluthiacet-methyl, isopropazol, sulfentrazone, thidiazimin, azafenidin, pyraflufen-ethyl, cinidon-ethyl, difenzoquat, diquat, paraquat, 2,4-D, 2,4-DB, clopyralid, dicamba, fluroxypyr, MCPA, MCPB, mecoprop, quinclorac, triclopyr, azimsulfuiron, bensulfuron-methyl, chlorimuron-ethyl, chlorsulfuron, cloransulam-methyl, cyclosulfamuron, diclosulam, ethoxysulfuron, flazasulfuron, flucarbazone, flumetsulam, flupyrsulfuron, halosulfuron-methyl, imazosulfuron, indosulfuron, metosulam, metsulfuron-methyl, nicosulfuron, oxasulfuron, primisulfuron-methyl, procarbazone-sodium, prosulfuron, pyrazosulfuron-ethyl, rimsulfuron, sulfometuron-methyl, sulfosulfuron, triasulfuron, tribenuron-methyl, tritosulfuron, thifensulfuron-methyl, triflusulfuron-methyl, pyribenzoxim, -bispyribac-sodium, pyriminobac-methyl, pyrithiobac-sodium, imazameth, imazamethabenz-methyl, imazamox, imazapic, imazapyr, imazaquin, imazethapyr, tepraloxydim, alloxydim-sodium, clethodim, clodinafop-propargyl, cyhalofop-butyl, dichlofop-methyl, fenoxaprop-ethyl, fenoxaprop-p-ethyl, fluazifop-buthyl, fluazifop-p-butyl, haloxyfop-methyl, quizalofop-p-ethyl, sethoxydim, tralkoxydim, diflufenican, flurtamone, norflurazone, benzofenap, isoxaflutole, pyrazolate, pyrazoxyfen, sulcotrione, clomazone, mesotrione, isoxachlortole, bialaphos, glufosinate-ammonium, glyphosate, sulfosate, dichlobenil, isoxaben, benthiocarb, butylate, dimepiperate, EPTC, esprocarb, molinate, pyributicarb, triallate, diflufenzopyr, bromobutide, DSMA, MSMA, cafenstrol, daimron, epoprodan, flupoxam, metobenzuron, pentoxazone, piperophos, triaziflam, beflubutamid, benzobicyclon, clomeprop, fentrazamide, flufenacet, florasulam, indanofan, isoxadifen, mesotrione, naploanilide, oxaziclomefone, pethoxyamid, phnothiol, and pyridafol The above compounds are described in the catalog of Farm Chemicals Handbook, 1995 (Meister Publishing Company); AG CHEM NEW COMPOUND REVIEW, VOL. 13, 1995; VOL. 15, 1997; or VOL. 16, 1998, AGROW No. 296 p22, No. 297 p21, No. 308 p22, or No. 324 p26-27, or Josouzai Kenkyu Souran (Hakuyu-sha).

When the compounds of the invention are used as the active ingredients of herbicides, the application amount, although it may vary with the weather conditions, formulation types, application times, application methods, soil conditions, crops to be protected, and weeds to be controlled, etc. is usually in the range of about 0.01 to about 20,000 g, preferably about 1 to about 12,000 g, per hectare. In the case of emulsifiable concentrates, wettable powders, flowables, concentrated emulsions, water-dispersible granules, or the like, containing the compound of the invention, they are usually applied after being diluted in their prescribed amounts with water (if necessary, containing an adjuvant such as a spreading agent) at a ratio of about 10 to 1000 liters per hectare. In the case of granules or some types of flowables, containing the compound of the invention, they are usually applied as such without any dilution. The adjuvant which can be used, if necessary, may include, in addition to the surfactants as described above, polyoxyethylene resin acids (esters), lignin sulfonates, abietates, dinaphthylmethanedisulfonates, crop oil concentrates, and vegetable oils such as soybean oil, corn oil, cottonseed oil, and sunflower oil.

The compounds of the invention can also be used as the active ingredients of harvesting aids such as defoliants and desiccants for cotton, desiccants for potato (*Solanum tuberosum*) and the like. In these cases, the compounds of the invention are usually formulated in the same manner as when they are used as the active ingredients of herbicides, and may be used alone or in admixture with other harvesting aids for foliar treatment before the harvesting of crops.

EXAMPLE

The invention is described below in more detail with reference to Production Examples, Formulation Examples and Test Examples, but the invention is not limited to these Examples.

First, Production Examples for the compounds of the invention are described. Compound numbers for the compounds of the invention are Numbers appeared in Tables 1 to Tables 3 described later.

Production Example 1 [Production of Compound 1-1]

Step 1)

Into 100 ml of anhydrous diethyl ether was dissolved 1.5 g of methyl 2-[4-(hydroxymethyl)phenoxy]propionate; 0.71 g of phosphorus tribromide was added dropwise under ice-cooling and stirring, and the mixture was stirred for 2 hours at room temperature. The reaction solution was poured into ice water and the mixture was stirred; then the mixture was phase-separated to a diethyl ether layer and an aqueous layer, and the aqueous layer was extracted once with diethyl ether. Organic layers were combined and washed once with water, twice with saturated aqueous sodium hydrogen carbonate solution and once with saturated aqueous sodium chloride solution, dried over magnesium sulfate and concentrated under reduced pressure. The obtained residue was used in the following step as it was.

Step 2)

Into 25 ml of N,N-dimethylformamide was dissolved 2.42 g of 2-chloro-4-fluoro-5-[3-methyl-2,6-dioxo-4-(trifluoromethyl)-1,2,3,6-tetrahydropyrimidine-1-yl]phenol; 1.18 g of anhydrous potassium carbonate was added; the residue obtained in the above step 1 was added at room temperature under stirring and the mixture was stirred for 7 hours at room temperature. The reaction solution was poured into a mixture of ice and a saturated aqueous ammonium chloride solution and the mixture was extracted twice with ethyl acetate. The organic layers were combined and washed once with a saturated aqueous ammonium chloride solution, once with water, twice with 10% aqueous potassium carbonate solution, twice with water, once with 0.1N hydrochloric acid and once with saturated aqueous sodium chloride solution in turn, dried over magnesium sulfate and then concentrated under reduced pressure. The obtained residue was subjected to silica gel column chromatography to give 2.98 g of methyl 2-[4-({2-chloro-4-fluoro-5-[3-methyl-2,6-dioxo-4-(trifluoromethyl)-1,2,3,6-tetrahydropyrimidine-1-yl]phenoxyl}methyl)phenoxy]propionate [Compound 1-1].

mp.: 126.8° C.

Production Example 2 [Production of Compound 2-1]

Into 10 ml of anhydrous tetrahydrofuran were dissolved 0.3 g of 2-chloro-4-fluoro-5-[3-methyl-2,6-dioxo-4-(trifluoromethyl)-1,2,3,6-tetrahydropyrimidine-1-yl]phenol, 0.186 g of methyl 2-[3-(hydroxymethyl)phenoxy]propionate and 0.232 g of triphenylphosphine; 0.179 g of diisopropyl azodicarboxylate was added dropwise under ice-cooling and stirring and the mixture was stirred overnight at room temperature. The reaction solution was concentrated under reduced pressure; the obtained residue was subjected to silica gel column chromatography to give 0.166 g of methyl 2-[3-({2-chloro-4-fluoro-5-[3-methyl-2,6-dioxo-4-(trifluoromethyl)-1,2,3,6-tetrahydropyrimidine-1-yl]phenoxy}methyl)phenoxy]propionate [Compound 2-1].

$n_D^{32.3}$: 1.5402

Production Example 3 [Production of Compound 3-2]

Into 10 ml of N,N-dimethylformamide was dissolved 0.3 g of 2-chloro-4-fluoro-5-[3-methyl-2,6-dioxo-4-(trifluoromethyl)-1,2,3,6-tetrahydropyrimidine-1-yl]phenol; 0.159 g of anhydrous potassium carbonate was added; 0.305 g of ethyl 2-[2-(bromomethyl)phenoxy]propionate was added at room temperature under stirring and the mixture was stirred overnight at room temperature. The reaction solution was poured into a mixture of ice and a saturated aqueous ammonium chloride solution and the mixture was extracted twice with ethyl acetate. The organic layers were combined and washed once with a saturated aqueous ammonium chloride solution and once with saturated aqueous sodium chloride solution in turn, dried over magnesium sulfate and then concentrated under reduced pressure. The obtained residue was subjected to silica gel column chromatography to give 0.35 g of ethyl 2-[2-({2-chloro-4-fluoro-5-[3-methyl-2,6-dioxo-4-(trifluoromethyl)-1,2,3,6-tetrahydropyrimidine-1-yl]phenoxy}methyl)phenoxy]propionate [Compound 3-2].

$n_D^{23.8}$: 1.5404

Production Example 4 [Production of Compound 3-1]

Into 10 ml of methanol was dissolved 0.216 g of ethyl 2-[2-({2-chloro-4-fluoro-5-[3-methyl-2,6-dioxo-4-

(trifluoromethyl)-1,2,3,6-tetrahydropyrimidine-1-yl]phenoxy}methyl)phenoxy]propionate obtained in the above-described Production Example 3; a catalytic amount of sodium methoxide was added under ice-cooling and stirring and the mixture was stirred for 6 hours at room temperature. The reaction solution was poured into 1N hydrochloric acid and the mixture was extracted twice with ethyl acetate. The organic layers were combined and washed once with a saturated aqueous sodium chloride solution, dried over magnesium sulfate and then concentrated under reduced pressure to give 0.193 g of methyl 2-[2-({2-chloro-4-fluoro-5-[3-methyl-2,6-dioxo-4-(trifluoromethyl)-1,2,3,6-tetrahydropyrimidine-1-yl]phenoxy}methyl)phenoxy]propionate [Compound 3-1].

$n_D^{237}$: 1.5442

Production Example 5 [Production of Compound 2-21]

Into 10 ml of anhydrous tetrahydrofuran were dissolved 0.3 g of 2-chloro-4-fluoro-5-[3-methyl-2,6-dioxo-4-(trifluoromethyl)-1,2,3,6-tetrahydropyrimidine-1-yl]phenol, 0.199 g of methyl 2-[3-(1-hydroxyethyl)phenoxy]propionate and 0.232 g of triphenylphosphine; 0.179 g of dilsopropyl azodicarboxylate was added dropwise under ice-cooling and stirring and the mixture was stirred overnight at room temperature. The reaction solution was concentrated under reduced pressure; the obtained residue was subjected to silica gel column chromatography to give methyl 2-[3-(1-{2-chloro-4-fluoro-5-[3-methyl-2,6-dioxo-4-(trifluoromethyl)-1,2,3,6-tetrahydropyrimidine-1-yl]phenoxy}ethyl)phenoxy]propionate [Compound 2-21].

$n_D^{259}$: 1.5298

Physical constants of the compounds of the invention produced in methods similar to those described in Production Example 1 to Production Example 5 are shown below:

Ethyl 2-[3-({2-chloro-4-fluoro-5-[3-methyl-2,6-dioxo-4-(trifluoromethyl)-1,2,3,6-tetrahydropyrimidine-1-yl]phenoxy}methyl)phenoxy]propionate [Compound 2-2].

$n_D^{25.9}$: 1.5429

Methyl 2-[2-({2-chloro-4-fluoro-5-[3-methyl-2,6-dioxo-4-(trifluoromethyl)-1,2,3,6-tetrahydropyrimidine-1-yl]phenoxy}methyl)-5-ethylphenoxy]propionate [Compound 3-101].

$n_D^{23.6}$: 1.5403

Ethyl 2-[2-chloro-4-({2-chloro-4-fluoro-5-[3-methyl-2,6-dioxo-4-(trifluoromethyl)-1,2,3,6-tetrahydropyrimidine-1-yl]phenoxy}methyl)phenoxy]propionate [Compound 1-42].

$n_D^{48.3}$: 1.5409

Methyl 2-[3-({2-chloro-4-fluoro-5-[3-methyl-2,6-dioxo-4-(trifluoromethyl)-1,2,3,6-tetrahydropyrimidine-1-yl]phenoxy}methyl)phenoxy]acetate [Compound 2-11].

mp.: 159.3° C.

Methyl 2-[4-(1-{2-chloro-4-fluoro-5-[3-methyl-2,6-dioxo-4-(trifluoromethyl)-1,2,3,6-tetrahydropyrimidine-1-yl]phenoxy}ethyl)phenoxy]propionate [Compound 1-21].

$n_D^{345}$: 1.5315

Ethyl 2-[4-({2-chloro-4-fluoro-5-[3-methyl-2,6-dioxo-4-(trifluoromethyl)-1,2,3,6-tetrahydropyrimidine-1-yl]phenoxy}methyl)phenoxy]propionate [Compound 1-2].

mp.: 123.9° C.

Methyl 2-[5-({2-chloro-4-fluoro-5-[3-methyl-2,6-dioxo-4-(trifluoromethyl)-1,2,3,6-tetrahydropyrimidine-1-yl]phenoxy}methyl)-2-methoxyphenoxy]propionate [Compound 2-61].

$n_D^{49.4}$: 1.5422

Methyl 2-[4-({2-chloro-4-fluoro-5-[3-methyl-2,6-dioxo-4-(trifluoromethyl)-1,2,3,6-tetrahydropyrimidine-1-yl]phenoxy}methyl)-2-methoxyphenoxy]propionate [Compound 1-61].

mp.: 122.8° C.

Methyl 2-[2-chloro-5-({2-chloro-4-fluoro-5-[3-methyl-2,6-dioxo-4-(trifluoromethyl)-1,2,3,6-tetrahydropyrimidine-1-yl]phenoxy}methyl)phenoxy]propionate [Compound 2-41].

mp.: 59.6° C.

Methyl 2-[5-({2-chloro-4-fluoro-5-[3-methyl-2,6-dioxo-4-(trifluoromethyl)-1,2,3,6-tetrahydropyrimidine-1-yl]phenoxy}methyl)-2-methylphenoxy]propionate [Compound 2-101].

mp: 50.9° C.

Methyl 2-[4-({2-chloro-4-fluoro-5-[3-methyl-2,6-dioxo-4-(trifluoromethyl)-1,2,3,6-tetrahydropyrimidine-1-yl]phenoxy}methyl)-2-methylphenoxy]propionate [Compound 1-101].

$n_D^{48.4}$: 1.5370

Methyl 2-[2,4-dichloro-3-({2-chloro-4-fluoro-5-[3-methyl-2,6-dioxo-4-(trifluoromethyl)-1,2,3,6-tetrahydropyrimidine-1-yl]phenoxy}methyl)phenoxy]propionate [Compound 2-161].

$n_D^{50.1}$: 1.5485

Methyl 2-[4-chloro-3-({2-chloro-4-fluoro-5-[3-methyl -2,6-dioxo-4-(trifluoromethyl)-1,2,3,6-tetrahydropyrimidine-1-yl]phenoxy}methyl)phenoxy]propionate [Compound 2-187].

$n_D^{489}$: 1.5470

Methyl 2-[2-bromo-4-({2-chloro-4-fluoro-5-[3-methyl-2,6-dioxo-4-(trifluoromethyl)-1,2,3,6-tetrahydropyrimidine-1-yl]phenoxy}methyl)-6-methoxyphenoxy]propionate [Compound 1-161].

mp.: 157.8° C.

Methyl 2-{4-[{2-chloro-4-fluoro-5-[3-methyl-2,6-dioxo-4-(trifluoromethyl)-1,2,3,6-tetrahydropyrimidine-1-yl]phenoxy}(cyano)methyl]phenoxy}propionate [Compound 1-226].

$n_D^{49.9}$: 1.5363

Methyl 2-[4-({2-chloro-4-fluoro-5-[3-methyl-2,6-dioxo-4-(trifluoromethyl)-1,2,3,6-tetrahydropyrimidine-1-yl]phenoxy}methyl)-2,6-dimethoxyphenoxy]propionate [Compound 1-238].

mp.: 160.2° C.

Methyl 2-[4-(1-{2-chloro-4-fluoro-5-[3-methyl-2,6-dioxo-4-(trifluoromethyl)-1,2,3,6-tetrahydropyrimidine-1-yl]phenoxy}propyl)phenoxy]propionate [Compound 1-213].

$n_D^{35.0}$: 1.4729

Methyl 2-[4-({2-chloro-4-fluoro-5-[3-methyl-2,6-dioxo-4-(trifluoromethyl)-1,2,3,6-tetrahydropyrimidine-1-yl]phenoxy}(phenyl)methyl)phenoxy]propionate [Compound 1-246].

$n_D^{387}$: 1.5572

Methyl 2-[4-({2-chloro-4-fluoro-5-[3-methyl-2,6-dioxo-4-(trifluoromethyl)-1,2,3,6-tetrahydropyrimidine-1-yl]phenoxy}methyl)-3-fluorophenoxy]propionate [Compound 1-242].

mp.: 48.0° C.

Processes for producing starting compounds for the compounds of the invention are shown below as Reference Production Examples.

Reference Production Example 1 [Production of Methyl 2-3-(hydroxymethyl)phenoxy]propionate Step 1)

Into 150 ml of N,N-dimethylformamide was dissolved 10 g of 3-hydroxybenzaldehyde; 13.6 g of anhydrous potassium carbonate was added; 13.7 g of methyl 2-bromopropionate was added dropwise at room temperature under stirring and the mixture was stirred overnight at room temperature. The reaction solution was poured into ice water and the mixture was extracted twice with t-butyl methyl ether. The organic layer was washed once with 5N aqueous sodium hydroxide solution, twice with water, once with 0.1N hydrochloric acid and once with saturated aqueous sodium chloride solution in turn, dried over magnesium sulfate and then concentrated under reduced pressure to give 16.48 g of methyl 2-(3-formylphenoxy)propionate.

mp.: 50.7° C.

Step 2)

Into 100 ml of methanol was dissolved 52 mg of sodium methoxide; the solution was cooled to 5° C. To the solution was added 1 g of methyl 2-(3-formylphenoxy)propionate was added; after adding 55 mg of sodium borohydride below 8° C. under stirring, the mixture was stirred for 2 hours at the same temperature. The reaction solution was poured into ice-cooled 2N hydrochloric acid and the mixture was extracted twice with diethyl ether. The organic layers were combined, washed once with saturated aqueous sodium chloride solution, dried over magnesium sulfate and then concentrated under reduced pressure to give 0.921 g of methyl 2-[3-(hydroxymethyl)phenoxy]propionate.

$n_D^{25.1}$: 1.5175

Reference Production Example 2 [Production of Methyl 2-3-(hydroxymethyl)phenoxy]propionate Into 100 ml of ethyl acetate was dissolved 5.09 g of methyl 2-(3-formylphenoxy)propionate; 0.57 g of 10% palladium on carbon was added; the mixture was stirred for 30 minutes in a hydrogen atmosphere at atmospheric pressure. The reaction solution was filtered; the filtrate was concentrated and the residue was subjected to silica gel column chromatography to give 3.20 g of methyl 2-[3-(hydroxymethyl)phenoxy]propionate.

Reference Production Example 3 Production of Methyl 2-(2-chloro-5-methylphenoxy)propionate Step 1)

Into 100 ml of N,N-dimethylformamide was dissolved 3.7 g of 2-chloro-3-methylphenol; 4.3g of anhydrous potassium carbonate was added; 4.12 g of methyl 2-bromopropionate was added dropwise at room temperature under stirring and the mixture was stirred overnight at room temperature. The reaction solution was poured into ice water and the mixture was extracted with t-butyl methyl ether. The organic layer was washed once with 5N aqueous sodium hydroxide solution, twice with water, once with 0.1N hydrochloric acid and once with saturated aqueous sodium chloride solution in turn, dried over magnesium sulfate and then concentrated under reduced pressure to give 5.61 g of methyl 2-(2-chloro-5-methylphenoxy)propionate.

Step 2)

Into 150 ml of fluorobenzene was dissolved 5.61 g of methyl 2-(2-chloro-5-methylphenoxy)propionate obtained above; 4.37 g of N-bromosuccinimide and then 0.2 g of 1,1'-azobis(cyclohexanecarbonitrile) were added, and the mixture was stirred under reflux for 2 hours. After the reaction was completed, the solution was allowed to left for cooling; the reaction solution was filtered; the filtrate was concentrated under reduced pressure; and the residue was subjected to silica gel chromatography to give 6.59 g of methyl 2-[5-(bromomethyl)-2-chlorophenoxy]propionate.

$n_d^{25.6}$: 1.5480

Examples of the compounds of the invention are listed in Table 1 to Table 3 together with Compound numbers, but the invention is not limited to these examples.

TABLE 1

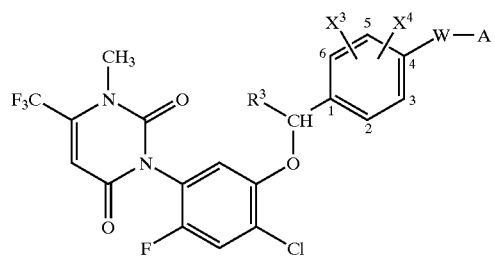

| Compound No. | $R^3$ | $X^3$ | $X^4$ | W | A |
|---|---|---|---|---|---|
| 1-1 | H | H | H | O | $CHMeCO_2Me$ |
| 1-2 | H | H | H | O | $CHMeCO_2Et$ |
| 1-3 | H | H | H | O | $CHMeCO_2Pr$ |
| 1-4 | H | H | H | O | $CHMeCO_2Bu$ |
| 1-5 | H | H | H | O | $CHMeCO_2CHMe_2$ |
| 1-6 | H | H | H | O | $CHMeCO_2CMe_3$ |

TABLE 1-continued

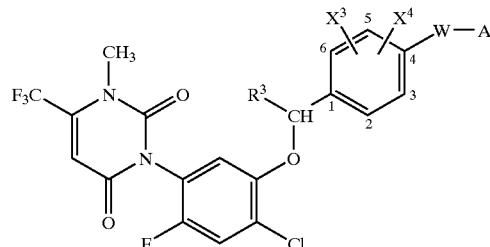

| Compound No. | R³ | X³ | X⁴ | W | A |
|---|---|---|---|---|---|
| 1-7 | H | H | H | O | CHMeCO$_2$CH$_2$CH$_2$F |
| 1-8 | H | H | H | O | CHMeCO$_2$CH$_2$CH$_2$Cl |
| 1-9 | H | H | H | O | CHMeCO$_2$CH$_2$CCl$_3$ |
| 1-10 | H | H | H | O | CHMeCO$_2$CH$_2$CH=CH$_2$ |
| 1-11 | H | H | H | O | CH$_2$CO$_2$Me |
| 1-12 | H | H | H | O | CH$_2$CO$_2$Et |
| 1-13 | H | H | H | O | CH$_2$CO$_2$Pr |
| 1-14 | H | H | H | O | CH$_2$CO$_2$Bu |
| 1-15 | H | H | H | O | CH$_2$CO$_2$CHMe$_2$ |
| 1-16 | H | H | H | O | CH$_2$CO$_2$CMe$_3$ |
| 1-17 | H | H | H | O | CH$_2$CO$_2$CH$_2$CH$_2$F |
| 1-18 | H | H | H | O | CH$_2$CO$_2$CH$_2$CH$_2$Cl |
| 1-19 | H | H | H | O | CH$_2$CO$_2$CH$_2$CCl$_3$ |
| 1-20 | H | H | H | O | CH$_2$CO$_2$CH$_2$CH=CH$_2$ |
| 1-21 | Me | H | H | O | CHMeCO$_2$Me |
| 1-22 | Me | H | H | O | CHMeCO$_2$Et |
| 1-23 | Me | H | H | O | CHMeCO$_2$Bu |
| 1-24 | Me | H | H | O | CHMeCO$_2$Pr |
| 1-25 | Me | H | H | O | CHMeCO$_2$CHMe$_2$ |
| 1-26 | Me | H | H | O | CHMeCO$_2$CMe$_3$ |
| 1-27 | Me | H | H | O | CHMeCO$_2$CH$_2$CH$_2$F |
| 1-28 | Me | H | H | O | CHMeCO$_2$CH$_2$CH$_2$Cl |
| 1-29 | Me | H | H | O | CHMeCO$_2$CH$_2$CCl$_3$ |
| 1-30 | Me | H | H | O | CHMeCO$_2$CH$_2$CH=CH$_2$ |
| 1-31 | Me | H | H | O | CH$_2$CO$_2$Me |
| 1-32 | Me | H | H | O | CH$_2$CO$_2$Et |
| 1-33 | Me | H | H | O | CH$_2$CO$_2$Pr |
| 1-34 | Me | H | H | O | CH$_2$CO$_2$Bu |
| 1-35 | Me | H | H | O | CH$_2$CO$_2$CHMe$_2$ |
| 1-36 | Me | H | H | O | CH$_2$CO$_2$CMe$_3$ |
| 1-37 | Me | H | H | O | CH$_2$CO$_2$CH$_2$CH$_2$F |
| 1-38 | Me | H | H | O | CH$_2$CO$_2$CH$_2$CH$_2$Cl |
| 1-39 | Me | H | H | O | CH$_2$CO$_2$CH$_2$CCl$_3$ |
| 1-40 | Me | H | H | O | CH$_2$CO$_2$CH$_2$CH=CH$_2$ |
| 1-41 | H | 3-Cl | H | O | CHMeCO$_2$Me |
| 1-42 | H | 3-Cl | H | O | CHMeCO$_2$Et |
| 1-43 | H | 3-Cl | H | O | CHMeCO$_2$Pr |
| 1-44 | H | 3-Cl | H | O | CHMeCO$_2$Bu |
| 1-45 | H | 3-Cl | H | O | CHMeCO$_2$CHMe$_2$ |
| 1-46 | H | 3-Cl | H | O | CHMeCO$_2$CMe$_3$ |
| 1-47 | H | 3-Cl | H | O | CHMeCO$_2$CH$_2$CH$_2$F |
| 1-48 | H | 3-Cl | H | O | CHMeCO$_2$CH$_2$CH$_2$Cl |
| 1-49 | H | 3-Cl | H | O | CHMeCO$_2$CH$_2$CCl$_3$ |
| 1-50 | H | 3-Cl | H | O | CHMeCO$_2$CH$_2$CH=CH$_2$ |
| 1-51 | H | 3-Cl | H | O | CH$_2$CO$_2$Me |
| 1-52 | H | 3-Cl | H | O | CH$_2$CO$_2$Et |
| 1-53 | H | 3-Cl | H | O | CH$_2$CO$_2$Pr |
| 1-54 | H | 3-Cl | H | O | CH$_2$CO$_2$Bu |
| 1-55 | H | 3-Cl | H | O | CH$_2$CO$_2$CHMe$_2$ |
| 1-56 | H | 3-Cl | H | O | CH$_2$CO$_2$CMe$_3$ |
| 1-57 | H | 3-Cl | H | O | CH$_2$CO$_2$CH$_2$CH$_2$F |
| 1-58 | H | 3-Cl | H | O | CH$_2$CO$_2$CH$_2$CH$_2$Cl |
| 1-59 | H | 3-Cl | H | O | CH$_2$CO$_2$CH$_2$CCl$_3$ |
| 1-60 | H | 3-Cl | H | O | CH$_2$CO$_2$CH$_2$CH=CH$_2$ |
| 1-61 | H | 3-OMe | H | O | CHMeCO$_2$Me |
| 1-62 | H | 3-OMe | H | O | CHMeCO$_2$Et |
| 1-63 | H | 3-OMe | H | O | CHMeCO$_2$Pr |
| 1-64 | H | 3-OMe | H | O | CHMeCO$_2$Bu |
| 1-65 | H | 3-OMe | H | O | CHMeCO$_2$CHMe$_2$ |
| 1-66 | H | 3-OMe | H | O | CHMeCO$_2$CMe$_3$ |
| 1-67 | H | 3-OMe | H | O | CHMeCO$_2$CH$_2$CH$_2$F |
| 1-68 | H | 3-OMe | H | O | CHMeCO$_2$CH$_2$CH$_2$Cl |
| 1-69 | H | 3-OMe | H | O | CHMeCO$_2$CH$_2$CCl$_3$ |
| 1-70 | H | 3-OMe | H | O | CHMeCO$_2$CH$_2$CH=CH$_2$ |

TABLE 1-continued

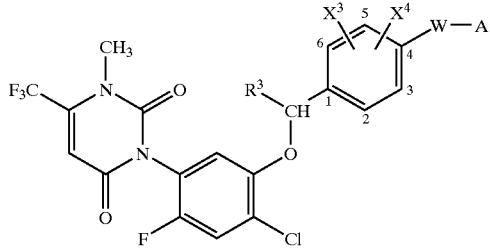

| Compound No. | $R^3$ | $X^3$ | $X^4$ | W | A |
|---|---|---|---|---|---|
| 1-71 | H | 3-OMe | H | O | $CH_2CO_2Me$ |
| 1-72 | H | 3-OMe | H | O | $CH_2CO_2Et$ |
| 1-73 | H | 3-OMe | H | O | $CH_2CO_2Pr$ |
| 1-74 | H | 3-OMe | H | O | $CH_2CO_2Bu$ |
| 1-75 | H | 3-OMe | H | O | $CH_2CO_2CHMe_2$ |
| 1-76 | H | 3-OMe | H | O | $CH_2CO_2CMe_3$ |
| 1-77 | H | 3-OMe | H | O | $CH_2CO_2CH_2CH_2F$ |
| 1-78 | H | 3-OMe | H | O | $CH_2CO_2CH_2CH_2Cl$ |
| 1-79 | H | 3-OMe | H | O | $CH_2CO_2CH_2CCl_3$ |
| 1-80 | H | 3-OMe | H | O | $CH_2CO_2CH_2CH=CH_2$ |
| 1-81 | Me | 3-Cl | H | O | $CHMeCO_2Me$ |
| 1-82 | Me | 3-Cl | H | O | $CHMeCO_2Et$ |
| 1-83 | Me | 3-Cl | H | O | $CHMeCO_2Pr$ |
| 1-84 | Me | 3-Cl | H | O | $CHMeCO_2Bu$ |
| 1-85 | Me | 3-Cl | H | O | $CHMeCO_2CHMe_2$ |
| 1-86 | Me | 3-Cl | H | O | $CHMeCO_2CMe_3$ |
| 1-87 | Me | 3-Cl | H | O | $CHMeCO_2CH_2CH_2F$ |
| 1-88 | Me | 3-Cl | H | O | $CHMeCO_2CH_2CH_2Cl$ |
| 1-89 | Me | 3-Cl | H | O | $CHMeCO_2CH_2CCl_3$ |
| 1-90 | Me | 3-Cl | H | O | $CHMeCO_2CH_2CH=CH_2$ |
| 1-91 | Me | 3-Cl | H | O | $CH_2CO_2Me$ |
| 1-92 | Me | 3-Cl | H | O | $CH_2CO_2Et$ |
| 1-93 | Me | 3-Cl | H | O | $CH_2CO_2Pr$ |
| 1-94 | Me | 3-Cl | H | O | $CH_2CO_2Bu$ |
| 1-95 | Me | 3-Cl | H | O | $CH_2CO_2CHMe_2$ |
| 1-96 | Me | 3-Cl | H | O | $CH_2CO_2CMe_3$ |
| 1-97 | Me | 3-Cl | H | O | $CH_2CO_2CH_2CH_2F$ |
| 1-98 | Me | 3-Cl | H | O | $CH_2CO_2CH_2CH_2Cl$ |
| 1-99 | Me | 3-Cl | H | O | $CH_2CO_2CH_2CCl_3$ |
| 1-100 | Me | 3-Cl | H | O | $CH_2CO_2CH_2CH=CH_2$ |
| 1-101 | H | 3-Me | H | O | $CHMeCO_2Me$ |
| 1-102 | H | 3-Me | H | O | $CHMeCO_2Et$ |
| 1-103 | H | 3-Me | H | O | $CHMeCO_2Pr$ |
| 1-104 | H | 3-Me | H | O | $CHMeCO_2Bu$ |
| 1-105 | H | 3-Me | H | O | $CHMeCO_2CHMe_2$ |
| 1-106 | H | 3-Me | H | O | $CHMeCO_2CMe_3$ |
| 1-107 | H | 3-Me | H | O | $CHMeCO_2CH_2CH_2F$ |
| 1-108 | H | 3-Me | H | O | $CHMeCO_2CH_2CH_2Cl$ |
| 1-109 | H | 3-Me | H | O | $CHMeCO_2CH_2CCl_3$ |
| 1-110 | H | 3-Me | H | O | $CHMeCO_2CH_2CH=CH_2$ |
| 1-111 | H | 3-Me | H | O | $CH_2CO_2Me$ |
| 1-112 | H | 3-Me | H | O | $CH_2CO_2Et$ |
| 1-113 | H | 3-Me | H | O | $CH_2CO_2Pr$ |
| 1-114 | H | 3-Me | H | O | $CH_2CO_2Bu$ |
| 1-115 | H | 3-Me | H | O | $CH_2CO_2CHMe_2$ |
| 1-116 | H | 3-Me | H | O | $CH_2CO_2CMe_3$ |
| 1-117 | H | 3-Me | H | O | $CH_2CO_2CH_2CH_2F$ |
| 1-118 | H | 3-Me | H | O | $CH_2CO_2CH_2CH_2Cl$ |
| 1-119 | H | 3-Me | H | O | $CH_2CO_2CH_2CCl_3$ |
| 1-120 | H | 3-Me | H | O | $CH_2CO_2CH_2CH=CH_2$ |
| 1-121 | H | 2-Me | 6-Me | O | $CHMeCO_2Me$ |
| 1-122 | H | 2-Me | 6-Me | O | $CHMeCO_2Et$ |
| 1-123 | H | 2-Me | 6-Me | O | $CHMeCO_2Pr$ |
| 1-124 | H | 2-Me | 6-Me | O | $CHMeCO_2Bu$ |
| 1-125 | H | 2-Me | 6-Me | O | $CHMeCO_2CHMe_2$ |
| 1-126 | H | 2-Me | 6-Me | O | $CHMeCO_2CMe_3$ |
| 1-127 | H | 2-Me | 6-Me | O | $CHMeCO_2CH_2CH_2F$ |
| 1-128 | H | 2-Me | 6-Me | O | $CHMeCO_2CH_2CH_2Cl$ |
| 1-129 | H | 2-Me | 6-Me | O | $CHMeCO_2CH_2CCl_3$ |
| 1-130 | H | 2-Me | 6-Me | O | $CHMeCO_2CH_2CH=CH_2$ |
| 1-131 | H | 2-Me | 6-Me | O | $CH_2CO_2Me$ |
| 1-132 | H | 2-Me | 6-Me | O | $CH_2CO_2Et$ |
| 1-133 | H | 2-Me | 6-Me | O | $CH_2CO_2Pr$ |
| 1-134 | H | 2-Me | 6-Me | O | $CH_2CO_2Bu$ |

TABLE 1-continued

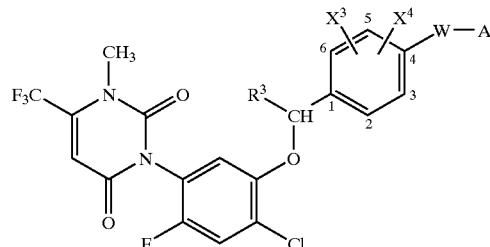

| Compound No. | $R^3$ | $X^3$ | $X^4$ | W | A |
|---|---|---|---|---|---|
| 1-135 | H | 2-Me | 6-Me | O | $CH_2CO_2CHMe_2$ |
| 1-136 | H | 2-Me | 6-Me | O | $CH_2CO_2CMe_3$ |
| 1-137 | H | 2-Me | 6-Me | O | $CH_2CO_2CH_2CH_2F$ |
| 1-138 | H | 2-Me | 6-Me | O | $CH_2CO_2CH_2CH_2Cl$ |
| 1-139 | H | 2-Me | 6-Me | O | $CH_2CO_2CH_2CCl_3$ |
| 1-140 | H | 2-Me | 6-Me | O | $CH_2CO_2CH_2CH=CH_2$ |
| 1-141 | H | 3-Me | 5-Me | O | $CHMeCO_2Me$ |
| 1-142 | H | 3-Me | 5-Me | O | $CHMeCO_2Et$ |
| 1-143 | H | 3-Me | 5-Me | O | $CHMeCO_2Pr$ |
| 1-144 | H | 3-Me | 5-Me | O | $CHMeCO_2Bu$ |
| 1-145 | H | 3-Me | 5-Me | O | $CHMeCO_2CHMe_2$ |
| 1-146 | H | 3-Me | 5-Me | O | $CHMeCO_2CMe_3$ |
| 1-147 | H | 3-Me | 5-Me | O | $CHMeCO_2CH_2CH_2F$ |
| 1-148 | H | 3-Me | 5-Me | O | $CHMeCO_2CH_2CH_2Cl$ |
| 1-149 | H | 3-Me | 5-Me | O | $CHMeCO_2CH_2CCl_3$ |
| 1-150 | H | 3-Me | 5-Me | O | $CHMeCO_2CH_2CH=CH_2$ |
| 1-151 | H | 3-Me | 5-Me | O | $CH_2CO_2Me$ |
| 1-152 | H | 3-Me | 5-Me | O | $CH_2CO_2Et$ |
| 1-153 | H | 3-Me | 5-Me | O | $CH_2CO_2Pr$ |
| 1-154 | H | 3-Me | 5-Me | O | $CH_2CO_2Bu$ |
| 1-155 | H | 3-Me | 5-Me | O | $CH_2CO_2CHMe_2$ |
| 1-156 | H | 3-Me | 5-Me | O | $CH_2CO_2CMe_3$ |
| 1-157 | H | 3-Me | 5-Me | O | $CH_2CO_2CH_2CH_2F$ |
| 1-158 | H | 3-Me | 5-Me | O | $CH_2CO_2CH_2CH_2Cl$ |
| 1-159 | H | 3-Me | 5-Me | O | $CH_2CO_2CH_2CCl_3$ |
| 1-160 | H | 3-Me | 5-Me | O | $CH_2CO_2CH_2CH=CH_2$ |
| 1-161 | H | 3-Br | 5-OMe | O | $CHMeCO_2Me$ |
| 1-162 | H | 3-Br | 5-OMe | O | $CHMeCO_2Et$ |
| 1-163 | H | 3-Br | 5-OMe | O | $CHMeCO_2Pr$ |
| 1-164 | H | 3-Br | 5-OMe | O | $CHMeCO_2Bu$ |
| 1-165 | H | 3-Br | 5-OMe | O | $CHMeCO_2CHMe_2$ |
| 1-166 | H | 3-Br | 5-OMe | O | $CHMeCO_2CMe_3$ |
| 1-167 | H | 3-Br | 5-OMe | O | $CHMeCO_2CH_2CH_2F$ |
| 1-168 | H | 3-Br | 5-OMe | O | $CHMeCO_2CH_2CH_2Cl$ |
| 1-169 | H | 3-Br | 5-OMe | O | $CHMeCO_2CH_2CCl_3$ |
| 1-170 | H | 3-Br | 5-OMe | O | $CHMeCO_2CH_2CH=CH_2$ |
| 1-171 | H | 3-Br | 5-OMe | O | $CH_2CO_2Me$ |
| 1-172 | H | 3-Br | 5-OMe | O | $CH_2CO_2Et$ |
| 1-173 | H | 3-Br | 5-OMe | O | $CH_2CO_2Pr$ |
| 1-174 | H | 3-Br | 5-OMe | O | $CH_2CO_2Bu$ |
| 1-175 | H | 3-Br | 5-OMe | O | $CH_2CO_2CHMe_2$ |
| 1-176 | H | 3-Br | 5-OMe | O | $CH_2CO_2CMe_3$ |
| 1-177 | H | 3-Br | 5-OMe | O | $CH_2CO_2CH_2CH_2F$ |
| 1-178 | H | 3-Br | 5-OMe | O | $CH_2CO_2CH_2CH_2Cl$ |
| 1-179 | H | 3-Br | 5-OMe | O | $CH_2CO_2CH_2CCl_3$ |
| 1-180 | H | 3-Br | 5-OMe | O | $CH_2CO_2CH_2CH=CH_2$ |
| 1-181 | H | H | H | O | $CH_2CH_2CH_2CO_2CH_3$ |
| 1-182 | H | H | H | O | $CHEtCO_2CH_3$ |
| 1-183 | H | H | H | O | $CH_2CH_2CH_2CH_2CO_2Me$ |
| 1-184 | Me | 3-Br | 5-OMe | O | $CHMeCO_2Me$ |
| 1-185 | Me | 2-Me | H | O | $CHMeCO_2Me$ |
| 1-186 | Me | 2-Me | 6-Me | O | $CHMeCO_2Me$ |
| 1-187 | H | 3-I | 5-OMe | O | $CHMeCO_2Me$ |
| 1-188 | H | 3-OEt | H | O | $CHMeCO_2Et$ |
| 1-189 | H | 3-OEt | H | O | $CHMeCO_2Me$ |
| 1-190 | Me | 3-Me | H | O | $CHMeCO_2Me$ |
| 1-191 | Me | 3-Me | H | O | $CHMeCO_2Et$ |
| 1-192 | Me | 3-Me | H | O | $CHMeCO_2Pr$ |
| 1-193 | Me | 3-Me | H | O | $CHMeCO_2Bu$ |
| 1-194 | Me | 3-Me | H | O | $CHMeCO_2CHMe_2$ |
| 1-195 | Me | 3-Me | H | O | $CHMeCO_2CMe_3$ |
| 1-196 | Me | 3-Me | H | O | $CHMeCO_2CH_2CH_2F$ |
| 1-197 | Me | 3-Me | H | O | $CHMeCO_2CH_2CH_2Cl$ |
| 1-198 | Me | 3-Me | H | O | $CHMeCO_2CH_2CCl_3$ |

TABLE 1-continued

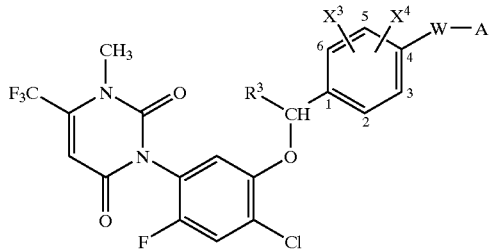

| Compound No. | R³ | X³ | X⁴ | W | A |
| --- | --- | --- | --- | --- | --- |
| 1-199 | Me | 3-Me | H | O | CHMeCO₂CH₂CH=CH₂ |
| 1-200 | Me | 3-Me | H | O | CH₂CO₂Bu |
| 1-201 | Me | 3-Me | H | O | CH₂CO₂Me |
| 1-202 | Me | 3-Me | H | O | CH₂CO₂Et |
| 1-203 | Me | 3-Me | H | O | CH₂CO₂Pr |
| 1-204 | Me | 3-Me | H | O | CH₂CO₂CHMe₂ |
| 1-205 | Me | 3-Me | H | O | CH₂CO₂CMe₃ |
| 1-206 | Me | 3-Me | H | O | CH₂CO₂CH₂CH₂F |
| 1-207 | Me | 3-Me | H | O | CH₂CO₂CH₂CH₂Cl |
| 1-208 | Me | 3-Me | H | O | CH₂CO₂CH₂CCl₃ |
| 1-209 | Me | 3-Me | H | O | CH₂CO₂CH₂CH=CH₂ |
| 1-210 | Et | H | H | O | CH₂CO₂Me |
| 1-211 | Et | H | H | O | CH₂CO₂Et |
| 1-212 | Et | H | H | O | CH₂CO₂Pr |
| 1-213 | Et | H | H | O | CHMeCO₂Me |
| 1-214 | Et | H | H | O | CHMeCO₂Et |
| 1-215 | Et | H | H | O | CHMeCO₂CH₂CH₂CH₃ |
| 1-216 | Et | H | H | O | CH₂CO₂CH₂CH=CH₂ |
| 1-217 | Et | H | H | O | CHMeCO₂CH₂CH=CH₂ |
| 1-218 | CF₃ | H | H | O | CH₂CO₂Me |
| 1-219 | CF₃ | H | H | O | CH₂CO₂Et |
| 1-220 | CF₃ | H | H | O | CH₂CO₂Pr |
| 1-221 | CF₃ | H | H | O | CHMeCO₂Me |
| 1-222 | CF₃ | H | H | O | CHMeCO₂Et |
| 1-223 | CF₃ | H | H | O | CHMeCO₂Pr |
| 1-224 | CF₃ | H | H | O | CH₂CO₂CH₂CH=CH₂ |
| 1-225 | CF₃ | H | H | O | CHMeCO₂CH₂CH=CH₂ |
| 1-226 | CN | H | H | O | CHMeCO₂Me |
| 1-227 | CN | H | H | O | CHMeCO₂Et |
| 1-228 | CN | H | H | O | CHMeCO₂Pr |
| 1-229 | CN | H | H | O | CHMeCO₂Bu |
| 1-230 | CN | H | H | O | CHMeCO₂CHMe₂ |
| 1-231 | CN | H | H | O | CHMeCO₂CMe₃ |
| 1-232 | CN | H | H | O | CHMeCO₂CH₂CH₂F |
| 1-233 | CN | H | H | O | CHMeCO₂CH₂CH₂Cl |
| 1-234 | CN | H | H | O | CHMeCO₂CH₂CCl₃ |
| 1-235 | CN | H | H | O | CHMeCO₂CH₂CH=CH₂ |
| 1-236 | CN | H | H | O | CH₂CO₂Me |
| 1-237 | CN | H | H | O | CH₂CO₂Et |
| 1-238 | H | 3-OMe | 5-OMe | O | CHMeCO₂Me |
| 1-239 | H | 3-OMe | 5-OMe | O | CHMeCO₂Et |
| 1-240 | H | 3-OMe | 5-OMe | O | CH₂CO₂Me |
| 1-241 | H | 3-OMe | 5-OMe | O | CH₂CO₂Et |
| 1-242 | H | 2-F | H | O | CHMeCO₂Me |
| 1-243 | H | 2-F | H | O | CHMeCO₂Et |
| 1-244 | H | 2-F | H | O | CH₂CO₂Me |
| 1-245 | H | 2-F | H | O | CH₂CO₂Et |
| 1-246 | Ph | H | H | O | CHMeCO₂Me |
| 1-247 | Ph | H | H | O | CHMeCO₂Et |
| 1-248 | Ph | H | H | O | CHMeCO₂CH₂CH₂CH₃ |
| 1-249 | Ph | H | H | O | CH₂CO₂Me |
| 1-250 | Ph | H | H | O | CH₂CO₂Et |
| 1-251 | H | H | H | S | CHMeCO₂Me |
| 1-252 | H | H | H | S | CHMeCO₂Et |
| 1-253 | H | H | H | S | CHMeCO₂Pr |
| 1-254 | H | H | H | S | CHMeCO₂Bu |
| 1-255 | H | H | H | S | CHMeCO₂CHMe₂ |
| 1-256 | H | H | H | S | CHMeCO₂CMe₃ |
| 1-257 | H | H | H | S | CHMeCO₂CH₂CH₂F |
| 1-258 | H | H | H | S | CHMeCO₂CH₂CH₂Cl |
| 1-259 | H | H | H | S | CHMeCO₂CH₂CCl₃ |
| 1-260 | H | H | H | S | CHMeCO₂CH₂CH=CH₂ |
| 1-261 | H | H | H | S | CH₂CO₂Me |
| 1-262 | H | H | H | S | CH₂CO₂Et |

TABLE 1-continued

[Chemical structure: pyrimidine-2,4-dione with N-CH3, F3C, attached to phenyl ring bearing F and Cl, with OCH(R³) linker to phenyl ring (positions 1-6) with X³ at 6, X⁴ at 4, and W-A substituent]

| Compound No. | R³ | X³ | X⁴ | W | A |
|---|---|---|---|---|---|
| 1-263 | H | H | H | S | CH₂CO₂Pr |
| 1-264 | H | H | H | S | CH₂CO₂Bu |
| 1-265 | H | H | H | S | CH₂CO₂CHMe₂ |
| 1-266 | H | H | H | S | CH₂CO₂CMe₃ |
| 1-267 | H | H | H | S | CH₂CO₂CH₂CH₂F |
| 1-268 | H | H | H | S | CH₂CO₂CH₂CH₂Cl |
| 1-269 | H | H | H | S | CH₂CO₂CH₂CCl₃ |
| 1-270 | H | H | H | S | CH₂CO₂CH₂CH=CH₂ |
| 1-271 | Me | H | H | S | CHMeCO₂Me |
| 1-272 | Me | H | H | S | CHMeCO₂Et |
| 1-273 | Me | H | H | S | CHMeCO₂Pr |
| 1-274 | Me | H | H | S | CH₂CO₂Me |
| 1-275 | Me | H | H | S | CH₂CO₂Et |
| 1-276 | Pr | H | H | O | CH₂CO₂Me |
| 1-277 | Pr | H | H | O | CH₂CO₂Et |
| 1-278 | Pr | H | H | O | CH₂CO₂Pr |
| 1-279 | Pr | H | H | O | CH₂CO₂CHMe₂ |
| 1-280 | Pr | H | H | O | CH₂CO₂CMe₃ |
| 1-281 | Pr | H | H | O | CH₂CO₂CH₂CH₂F |
| 1-282 | Pr | H | H | O | CH₂CO₂CH₂CH₂Cl |
| 1-283 | Pr | H | H | O | CH₂CO₂CH₂CCl₃ |
| 1-284 | Pr | H | H | O | CH₂CO₂CH₂CH=CH₂ |

TABLE 2

[Chemical structure: similar pyrimidine-2,4-dione scaffold with phenoxy linker to phenyl ring having X³ at position 6, X⁴ at position 4, and W-A at position 3]

| Compound No. | R³ | X³ | X⁴ | W | A |
|---|---|---|---|---|---|
| 2-1 | H | H | H | O | CHMeCO₂Me |
| 2-2 | H | H | H | O | CHMeCO₂Et |
| 2-3 | H | H | H | O | CHMeCO₂Pr |
| 2-4 | H | H | H | O | CHMeCO₂Bu |
| 2-5 | H | H | H | O | CHMeCO₂CHMe₂ |
| 2-6 | H | H | H | O | CHMeCO₂CMe₃ |
| 2-7 | H | H | H | O | CHMeCO₂CH₂CH₂F |
| 2-8 | H | H | H | O | CHMeCO₂CH₂CH₂Cl |
| 2-9 | H | H | H | O | CHMeCO₂CH₂CCl₃ |
| 2-10 | H | H | H | O | CHMeCO₂CH₂CH=CH₂ |
| 2-11 | H | H | H | O | CH₂CO₂Me |
| 2-12 | H | H | H | O | CH₂CO₂Et |
| 2-13 | H | H | H | O | CH₂CO₂Pr |
| 2-14 | H | H | H | O | CH₂CO₂Bu |
| 2-15 | H | H | H | O | CH₂CO₂CHMe₂ |
| 2-16 | H | H | H | O | CH₂CO₂CMe₃ |
| 2-17 | H | H | H | O | CH₂CO₂CH₂CH₂F |
| 2-18 | H | H | H | O | CH₂CO₂CH₂CH₂Cl |
| 2-19 | H | H | H | O | CH₂CO₂CH₂CCl₃ |
| 2-20 | H | H | H | O | CH₂CO₂CH₂CH=CH₂ |
| 2-21 | Me | H | H | O | CHMeCO₂Me |
| 2-22 | Me | H | H | O | CHMeCO₂Et |

TABLE 2-continued

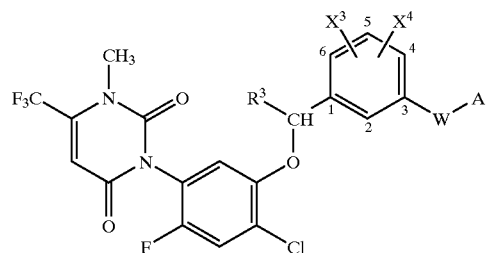

| Compound No. | $R^3$ | $X^3$ | $X^4$ | W | A |
|---|---|---|---|---|---|
| 2-23 | Me | H | H | O | CHMeCO$_2$Bu |
| 2-24 | Me | H | H | O | CHMeCO$_2$Pr |
| 2-25 | Me | H | H | O | CHMeCO$_2$CHMe$_2$ |
| 2-26 | Me | H | H | O | CHMeCO$_2$CMe$_3$ |
| 2-27 | Me | H | H | O | CHMeCO$_2$CH$_2$CH$_2$F |
| 2-28 | Me | H | H | O | CHMeCO$_2$CH$_2$CH$_2$Cl |
| 2-29 | Me | H | H | O | CHMeCO$_2$CH$_2$CCl$_3$ |
| 2-30 | Me | H | H | O | CHMeCO$_2$CH$_2$CH=CH$_2$ |
| 2-31 | Me | H | H | O | CH$_2$CO$_2$Me |
| 2-32 | Me | H | H | O | CH$_2$CO$_2$Et |
| 2-33 | Me | H | H | O | CH$_2$CO$_2$Pr |
| 2-34 | Me | H | H | O | CH$_2$CO$_2$Bu |
| 2-35 | Me | H | H | O | CH$_2$CO$_2$CHMe$_2$ |
| 2-36 | Me | H | H | O | CH$_2$CO$_2$CMe$_3$ |
| 2-37 | Me | H | H | O | CH$_2$CO$_2$CH$_2$CH$_2$F |
| 2-38 | Me | H | H | O | CH$_2$CO$_2$CH$_2$CH$_2$Cl |
| 2-39 | Me | H | H | O | CH$_2$CO$_2$CH$_2$CCl$_3$ |
| 2-40 | Me | H | H | O | CH$_2$CO$_2$CH$_2$CH=CH$_2$ |
| 2-41 | H | 4-Cl | H | O | CHMeCO$_2$Me |
| 2-42 | H | 4-Cl | H | O | CHMeCO$_2$Et |
| 2-43 | H | 4-Cl | H | O | CHMeCO$_2$Pr |
| 2-44 | H | 4-Cl | H | O | CHMeCO$_2$Bu |
| 2-45 | H | 4-Cl | H | O | CHMeCO$_2$CHMe$_2$ |
| 2-46 | H | 4-Cl | H | O | CHMeCO$_2$CMe$_3$ |
| 2-47 | H | 4-Cl | H | O | CHMeCO$_2$CH$_2$CH$_2$F |
| 2-48 | H | 4-Cl | H | O | CHMeCO$_2$CH$_2$CH$_2$Cl |
| 2-49 | H | 4-Cl | H | O | CHMeCO$_2$CH$_2$CCl$_3$ |
| 2-50 | H | 4-Cl | H | O | CHMeCO$_2$CH$_2$CH=CH$_2$ |
| 2-51 | H | 4-Cl | H | O | CH$_2$CO$_2$Me |
| 2-52 | H | 4-Cl | H | O | CH$_2$CO$_2$Et |
| 2-53 | H | 4-Cl | H | O | CH$_2$CO$_2$Pr |
| 2-54 | H | 4-Cl | H | O | CH$_2$CO$_2$Bu |
| 2-55 | H | 4-Cl | H | O | CH$_2$CO$_2$CHMe$_2$ |
| 2-56 | H | 4-Cl | H | O | CH$_2$CO$_2$CMe$_3$ |
| 2-57 | H | 4-Cl | H | O | CH$_2$CO$_2$CH$_2$CH$_2$F |
| 2-58 | H | 4-Cl | H | O | CH$_2$CO$_2$CH$_2$CH$_2$Cl |
| 2-59 | H | 4-Cl | H | O | CH$_2$CO$_2$CH$_2$CCl$_3$ |
| 2-60 | H | 4-Cl | H | O | CH$_2$CO$_2$CH$_2$CH=CH$_2$ |
| 2-61 | H | 4-OMe | H | O | CHMeCO$_2$Me |
| 2-62 | H | 4-OMe | H | O | CHMeCO$_2$Et |
| 2-63 | H | 4-OMe | H | O | CHMeCO$_2$Pr |
| 2-64 | H | 4-OMe | H | O | CHMeCO$_2$Bu |
| 2-65 | H | 4-OMe | H | O | CHMeCO$_2$CHMe$_2$ |
| 2-66 | H | 4-OMe | H | O | CHMeCO$_2$CMe$_3$ |
| 2-67 | H | 4-OMe | H | O | CHMeCO$_2$CH$_2$CH$_2$F |
| 2-68 | H | 4-OMe | H | O | CHMeCO$_2$CH$_2$CH$_2$Cl |
| 2-69 | H | 4-OMe | H | O | CHMeCO$_2$CH$_2$CCl$_3$ |
| 2-70 | H | 4-OMe | H | O | CHMeCO$_2$CH$_2$CH=CH$_2$ |
| 2-71 | H | 4-OMe | H | O | CH$_2$CO$_2$Me |
| 2-72 | H | 4-OMe | H | O | CH$_2$CO$_2$Et |
| 2-73 | H | 4-OMe | H | O | CH$_2$CO$_2$Pr |
| 2-74 | H | 4-OMe | H | O | CH$_2$CO$_2$Bu |
| 2-75 | H | 4-OMe | H | O | CH$_2$CO$_2$CHMe$_2$ |
| 2-76 | H | 4-OMe | H | O | CH$_2$CO$_2$CMe$_3$ |
| 2-77 | H | 4-OMe | H | O | CH$_2$CO$_2$CH$_2$CH$_2$F |
| 2-78 | H | 4-OMe | H | O | CH$_2$CO$_2$CH$_2$CH$_2$Cl |
| 2-79 | H | 4-OMe | H | O | CH$_2$CO$_2$CH$_2$CCl$_3$ |
| 2-80 | H | 4-OMe | H | O | CH$_2$CO$_2$CH$_2$CH=CH$_2$ |
| 2-81 | Me | 4-Cl | H | O | CHMeCO$_2$Me |
| 2-82 | Me | 4-Cl | H | O | CHMeCO$_2$Et |
| 2-83 | Me | 4-Cl | H | O | CHMeCO$_2$Pr |
| 2-84 | Me | 4-Cl | H | O | CHMeCO$_2$Bu |
| 2-85 | Me | 4-Cl | H | O | CHMeCO$_2$CHMe$_2$ |
| 2-86 | Me | 4-Cl | H | O | CHMeCO$_2$CMe$_3$ |

TABLE 2-continued

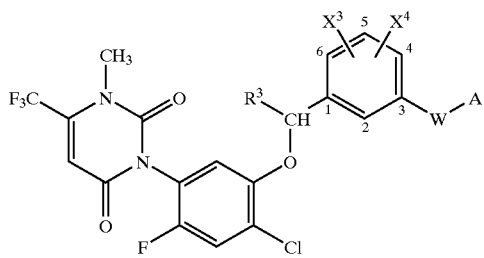

| Compound No. | $R^3$ | $X^3$ | $X^4$ | W | A |
|---|---|---|---|---|---|
| 2-87 | Me | 4-Cl | H | O | $CHMeCO_2CH_2CH_2F$ |
| 2-88 | Me | 4-Cl | H | O | $CHMeCO_2CH_2CH_2Cl$ |
| 2-89 | Me | 4-Cl | H | O | $CHMeCO_2CH_2CCl_3$ |
| 2-90 | Me | 4-Cl | H | O | $CHMeCO_2CH_2CH=CH_2$ |
| 2-91 | Me | 4-Cl | H | O | $CH_2CO_2Me$ |
| 2-92 | Me | 4-Cl | H | O | $CH_2CO_2Et$ |
| 2-93 | Me | 4-Cl | H | O | $CH_2CO_2Pr$ |
| 2-94 | Me | 4-Cl | H | O | $CH_2CO_2Bu$ |
| 2-95 | Me | 4-Cl | H | O | $CH_2CO_2CHMe_2$ |
| 2-96 | Me | 4-Cl | H | O | $CH_2CO_2CMe_3$ |
| 2-97 | Me | 4-Cl | H | O | $CH_2CO_2CH_2CH_2F$ |
| 2-98 | Me | 4-Cl | H | O | $CH_2CO_2CH_2CH_2Cl$ |
| 2-99 | Me | 4-Cl | H | O | $CH_2CO_2CH_2CCl_3$ |
| 2-100 | Me | 4-Cl | H | O | $CH_2CO_2CH_2CH=CH_2$ |
| 2-101 | H | 4-Me | H | O | $CHMeCO_2Me$ |
| 2-102 | H | 4-Me | H | O | $CHMeCO_2Et$ |
| 2-103 | H | 4-Me | H | O | $CHMeCO_2Pr$ |
| 2-104 | H | 4-Me | H | O | $CHMeCO_2Bu$ |
| 2-105 | H | 4-Me | H | O | $CHMeCO_2CHMe_2$ |
| 2-106 | H | 4-Me | H | O | $CHMeCO_2CMe_3$ |
| 2-107 | H | 4-Me | H | O | $CHMeCO_2CH_2CH_2F$ |
| 2-108 | H | 4-Me | H | O | $CHMeCO_2CH_2CH_2Cl$ |
| 2-109 | H | 4-Me | H | O | $CHMeCO_2CH_2CCl_3$ |
| 2-110 | H | 4-Me | H | O | $CHMeCO_2CH_2CH=CH_2$ |
| 2-111 | H | 4-Me | H | O | $CH_2CO_2Me$ |
| 2-112 | H | 4-Me | H | O | $CH_2CO_2Et$ |
| 2-113 | H | 4-Me | H | O | $CH_2CO_2Pr$ |
| 2-114 | H | 4-Me | H | O | $CH_2CO_2Bu$ |
| 2-115 | H | 4-Me | H | O | $CH_2CO_2CHMe_2$ |
| 2-116 | H | 4-Me | H | O | $CH_2CO_2CMe_3$ |
| 2-117 | H | 4-Me | H | O | $CH_2CO_2CH_2CH_2F$ |
| 2-118 | H | 4-Me | H | O | $CH_2CO_2CH_2CH_2Cl$ |
| 2-119 | H | 4-Me | H | O | $CH_2CO_2CH_2CCl_3$ |
| 2-120 | H | 4-Me | H | O | $CH_2CO_2CH_2CH=CH_2$ |
| 2-121 | H | 4-OMe | 5-OMe | O | $CHMeCO_2Me$ |
| 2-122 | H | 4-OMe | 5-OMe | O | $CHMeCO_2Et$ |
| 2-123 | H | 4-OMe | 5-OMe | O | $CHMeCO_2Pr$ |
| 2-124 | H | 4-OMe | 5-OMe | O | $CHMeCO_2Bu$ |
| 2-125 | H | 4-OMe | 5-OMe | O | $CHMeCO_2CHMe_2$ |
| 2-126 | H | 4-OMe | 5-OMe | O | $CHMeCO_2CMe_3$ |
| 2-127 | H | 4-OMe | 5-OMe | O | $CHMeCO_2CH_2CH_2F$ |
| 2-128 | H | 4-OMe | 5-OMe | O | $CHMeCO_2CH_2CH_2Cl$ |
| 2-129 | H | 4-OMe | 5-OMe | O | $CHMeCO_2CH_2CCl_3$ |
| 2-130 | H | 4-OMe | 5-OMe | O | $CHMeCO_2CH_2CH=CH_2$ |
| 2-131 | H | 4-OMe | 5-OMe | O | $CH_2CO_2Me$ |
| 2-132 | H | 4-OMe | 5-OMe | O | $CH_2CO_2Et$ |
| 2-133 | H | 4-OMe | 5-OMe | O | $CH_2CO_2Pr$ |
| 2-134 | H | 4-OMe | 5-OMe | O | $CH_2CO_2Bu$ |
| 2-135 | H | 4-OMe | 5-OMe | O | $CH_2CO_2CHMe_2$ |
| 2-136 | H | 4-OMe | 5-OMe | O | $CH_2CO_2CMe_3$ |
| 2-137 | H | 4-OMe | 5-OMe | O | $CH_2CO_2CH_2CH_2F$ |
| 2-138 | H | 4-OMe | 5-OMe | O | $CH_2CO_2CH_2CH_2Cl$ |
| 2-139 | H | 4-OMe | 5-OMe | O | $CH_2CO_2CH_2CCl_3$ |
| 2-140 | H | 4-OMe | 5-OMe | O | $CH_2CO_2CH_2CH=CH_2$ |
| 2-141 | H | 4-OMe | 5-Br | O | $CHMeCO_2Me$ |
| 2-142 | H | 4-OMe | 5-Br | O | $CHMeCO_2Et$ |
| 2-143 | H | 4-OMe | 5-Br | O | $CHMeCO_2Pr$ |
| 2-144 | H | 4-OMe | 5-Br | O | $CHMeCO_2Bu$ |
| 2-145 | H | 4-OMe | 5-Br | O | $CHMeCO_2CHMe_2$ |
| 2-146 | H | 4-OMe | 5-Br | O | $CHMeCO_2CMe_3$ |
| 2-147 | H | 4-OMe | 5-Br | O | $CHMeCO_2CH_2CH_2F$ |
| 2-148 | H | 4-OMe | 5-Br | O | $CHMeCO_2CH_2CH_2Cl$ |
| 2-149 | H | 4-OMe | 5-Br | O | $CHMeCO_2CH_2CCl_3$ |
| 2-150 | H | 4-OMe | 5-Br | O | $CHMeCO_2CH_2CH=CH_2$ |

TABLE 2-continued

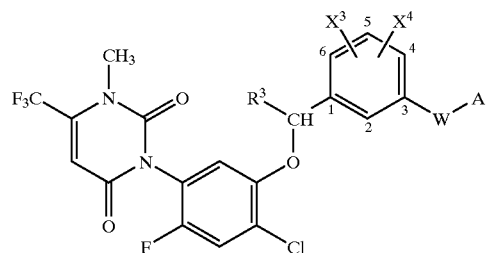

| Compound No. | $R^3$ | $X^3$ | $X^4$ | W | A |
|---|---|---|---|---|---|
| 2-151 | H | 4-OMe | 5-Br | O | $CH_2CO_2Me$ |
| 2-152 | H | 4-OMe | 5-Br | O | $CH_2CO_2Et$ |
| 2-153 | H | 4-OMe | 5-Br | O | $CH_2CO_2Pr$ |
| 2-154 | H | 4-OMe | 5-Br | O | $CH_2CO_2Bu$ |
| 2-155 | H | 4-OMe | 5-Br | O | $CH_2CO_2CHMe_2$ |
| 2-156 | H | 4-OMe | 5-Br | O | $CH_2CO_2CMe_3$ |
| 2-157 | H | 4-OMe | 5-Br | O | $CH_2CO_2CH_2CH_2F$ |
| 2-158 | H | 4-OMe | 5-Br | O | $CH_2CO_2CH_2CH_2Cl$ |
| 2-159 | H | 4-OMe | 5-Br | O | $CH_2CO_2CH_2CCl_3$ |
| 2-160 | H | 4-OMe | 5-Br | O | $CH_2CO_2CH_2CH=CH_2$ |
| 2-161 | H | 2-Cl | 6-Cl | O | $CHMeCO_2Me$ |
| 2-162 | H | 2-Cl | 6-Cl | O | $CHMeCO_2Et$ |
| 2-163 | H | 2-Cl | 6-Cl | O | $CHMeCO_2Pr$ |
| 2-164 | H | 2-Cl | 6-Cl | O | $CHMeCO_2Bu$ |
| 2-165 | H | 2-Cl | 6-Cl | O | $CHMeCO_2CHMe_2$ |
| 2-166 | H | 2-Cl | 6-Cl | O | $CHMeCO_2CMe_3$ |
| 2-167 | H | 2-Cl | 6-Cl | O | $CHMeCO_2CH_2CH_2F$ |
| 2-168 | H | 2-Cl | 6-Cl | O | $CHMeCO_2CH_2CH_2Cl$ |
| 2-169 | H | 2-Cl | 6-Cl | O | $CHMeCO_2CH_2CCl_3$ |
| 2-170 | H | 2-Cl | 6-Cl | O | $CHMeCO_2CH_2CH=CH_2$ |
| 2-171 | H | 2-Cl | 6-Cl | O | $CH_2CO_2Me$ |
| 2-172 | H | 2-Cl | 6-Cl | O | $CH_2CO_2Et$ |
| 2-173 | H | 2-Cl | 6-Cl | O | $CH_2CO_2Pr$ |
| 2-174 | H | 2-Cl | 6-Cl | O | $CH_2CO_2Bu$ |
| 2-175 | H | 2-Cl | 6-Cl | O | $CH_2CO_2CHMe_2$ |
| 2-176 | H | 2-Cl | 6-Cl | O | $CH_2CO_2CMe_3$ |
| 2-177 | H | 2-Cl | 6-Cl | O | $CH_2CO_2CH_2CH_2F$ |
| 2-178 | H | 2-Cl | 6-Cl | O | $CH_2CO_2CH_2CH_2Cl$ |
| 2-179 | H | 2-Cl | 6-Cl | O | $CH_2CO_2CH_2CCl_3$ |
| 2-180 | H | 2-Cl | 6-Cl | O | $CH_2CO_2CH_2CH=CH_2$ |
| 2-181 | H | H | H | O | $CH_2CH_2CH_2CO_2CH_3$ |
| 2-182 | H | H | H | O | $CHEtCO_2CH_3$ |
| 2-183 | H | H | H | O | $CH_2CH_2CH_2CH_2CO_2Me$ |
| 2-184 | Me | 2-Cl | 6-Cl | O | $CHMeCO_2Me$ |
| 2-185 | Me | 4-Me | H | O | $CHMeCO_2Me$ |
| 2-186 | Me | 4-OMe | 5-OMe | O | $CHMeCO_2Me$ |
| 2-187 | H | 6-Cl | H | O | $CHMeCO_2Me$ |
| 2-188 | H | 4-OEt | H | O | $CHMeCO_2Me$ |
| 2-189 | H | 6-F | H | O | $CHMeCO_2Me$ |
| 2-190 | Me | 4-Me | H | O | $CHMeCO_2Me$ |
| 2-191 | Me | 4-Me | H | O | $CHMeCO_2Et$ |
| 2-192 | Me | 4-Me | H | O | $CHMeCO_2Pr$ |
| 2-193 | Me | 4-Me | H | O | $CHMeCO_2Bu$ |
| 2-194 | Me | 4-Me | H | O | $CHMeCO_2CHMe_2$ |
| 2-195 | Me | 4-Me | H | O | $CHMeCO_2CMe_3$ |
| 2-196 | Me | 4-Me | H | O | $CHMeCO_2CH_2CH_2F$ |
| 2-197 | Me | 4-Me | H | O | $CHMeCO_2CH_2CH_2Cl$ |
| 2-198 | Me | 4-Me | H | O | $CHMeCO_2CH_2CCl_3$ |
| 2-199 | Me | 4-Me | H | O | $CHMeCO_2CH_2CH=CH_2$ |
| 2-200 | Me | 4-Me | H | O | $CH_2CO_2Bu$ |
| 2-201 | Me | 4-Me | H | O | $CH_2CO_2Me$ |
| 2-202 | Me | 4-Me | H | O | $CH_2CO_2Et$ |
| 2-203 | Me | 4-Me | H | O | $CH_2CO_2Pr$ |
| 2-204 | Me | 4-Me | H | O | $CH_2CO_2CHMe_2$ |
| 2-205 | Me | 4-Me | H | O | $CH_2CO_2CMe_3$ |
| 2-206 | Me | 4-Me | H | O | $CH_2CO_2CH_2CH_2F$ |
| 2-207 | Me | 4-Me | H | O | $CH_2CO_2CH_2CH_2Cl$ |
| 2-208 | Me | 4-Me | H | O | $CH_2CO_2CH_2CCl_3$ |
| 2-209 | Me | 4-Me | H | O | $CH_2CO_2CH_2CH=CH_2$ |
| 2-210 | Et | H | H | O | $CH_2CO_2Me$ |
| 2-211 | Et | H | H | O | $CH_2CO_2Et$ |
| 2-212 | Et | H | H | O | $CH_2CO_2Pr$ |
| 2-213 | Et | H | H | O | $CHMeCO_2Me$ |
| 2-214 | Et | H | H | O | $CHMeCO_2Et$ |

TABLE 2-continued

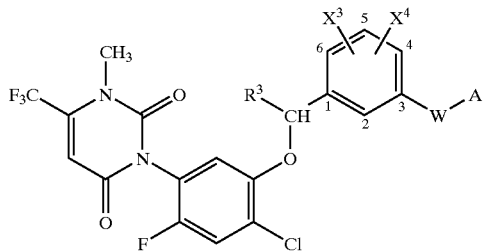

| Compound No. | $R^3$ | $X^3$ | $X^4$ | W | A |
|---|---|---|---|---|---|
| 2-215 | Et | H | H | O | CHMeCO$_2$Pr |
| 2-216 | Et | H | H | O | CH$_2$CO$_2$CH$_2$CH=CH$_2$ |
| 2-217 | Et | H | H | O | CHMeCO$_2$CH$_2$CH=CH$_2$ |
| 2-218 | CF$_3$ | H | H | O | CH$_2$CO$_2$Me |
| 2-219 | CF$_3$ | H | H | O | CH$_2$CO$_2$Et |
| 2-220 | CF$_3$ | H | H | O | CH$_2$CO$_2$Pr |
| 2-221 | CF$_3$ | H | H | O | CHMeCO$_2$Me |
| 2-222 | CF$_3$ | H | H | O | CHMeCO$_2$Et |
| 2-223 | CF$_3$ | H | H | O | CHMeCO$_2$Pr |
| 2-224 | CF$_3$ | H | H | O | CH$_2$CO$_2$CH$_2$CH=CH$_2$ |
| 2-225 | CF$_3$ | H | H | O | CHMeCO$_2$CH$_2$CH=CH$_2$ |
| 2-226 | H | H | H | S | CHMeCO$_2$Me |
| 2-227 | H | H | H | S | CHMeCO$_2$Et |
| 2-228 | H | H | H | S | CHMeCO$_2$Pr |
| 2-229 | H | H | H | S | CHMeCO$_2$Bu |
| 2-230 | H | H | H | S | CHMeCO$_2$CHMe$_2$ |
| 2-231 | H | H | H | S | CHMeCO$_2$CMe$_3$ |
| 2-232 | H | H | H | S | CHMeCO$_2$CH$_2$CH$_2$F |
| 2-233 | H | H | H | S | CHMeCO$_2$CH$_2$CH$_2$Cl |
| 2-234 | H | H | H | S | CHMeCO$_2$CH$_2$CCl$_3$ |
| 2-235 | H | H | H | S | CHMeCO$_2$CH$_2$CH=CH$_2$ |
| 2-236 | H | H | H | S | CH$_2$CO$_2$Me |
| 2-237 | H | H | H | S | CH$_2$CO$_2$Et |
| 2-238 | H | H | H | S | CH$_2$CO$_2$Pr |
| 2-239 | H | H | H | S | CH$_2$CO$_2$Bu |
| 2-240 | H | H | H | S | CH$_2$CO$_2$CHMe$_2$ |
| 2-241 | H | H | H | S | CH$_2$CO$_2$CMe$_3$ |
| 2-242 | H | H | H | S | CH$_2$CO$_2$CH$_2$CH$_2$F |
| 2-243 | H | H | H | S | CH$_2$CO$_2$CH$_2$CH$_2$Cl |
| 2-244 | H | H | H | S | CH$_2$CO$_2$CH$_2$CCl$_3$ |
| 2-245 | H | H | H | S | CH$_2$CO$_2$CH$_2$CH=CH$_2$ |
| 2-246 | Me | H | H | S | CHMeCO$_2$Me |
| 2-247 | Me | H | H | S | CHMeCO$_2$Et |
| 2-248 | Me | H | H | S | CHMeCO$_2$Pr |
| 2-249 | Me | H | H | S | CH$_2$CO$_2$Me |
| 2-250 | Me | H | H | S | CH$_2$CO$_2$Et |
| 2-251 | CN | H | H | O | CHMeCO$_2$Me |
| 2-252 | CN | H | H | O | CHMeCO$_2$Et |
| 2-253 | CN | H | H | O | CHMeCO$_2$Pr |
| 2-254 | CN | H | H | O | CHMeCO$_2$Bu |
| 2-255 | CN | H | H | O | CHMeCO$_2$CHMe$_2$ |
| 2-256 | CN | H | H | O | CHMeCO$_2$CMe$_3$ |
| 2-257 | CN | H | H | O | CHMeCO$_2$CH$_2$CH$_2$F |
| 2-258 | CN | H | H | O | CHMeCO$_2$CH$_2$CH$_2$Cl |
| 2-259 | CN | H | H | O | CHMeCO$_2$CH$_2$CCl$_3$ |
| 2-260 | CN | H | H | O | CHMeCO$_2$CH$_2$CH=CH$_2$ |
| 2-261 | CN | H | H | O | CH$_2$CO$_2$Me |
| 2-262 | CN | H | H | O | CH$_2$CO$_2$Et |
| 2-263 | Ph | H | H | O | CHMeCO$_2$Me |
| 2-264 | Ph | H | H | O | CHMeCO$_2$Et |
| 2-265 | Ph | H | H | O | CHMeCO$_2$CH$_2$CH$_2$CH$_3$ |
| 2-266 | Ph | H | H | O | CH$_2$CO$_2$Me |
| 2-267 | Ph | H | H | O | CH$_2$CO$_2$Et |
| 2-268 | Pr | H | H | O | CH$_2$CO$_2$Me |
| 2-269 | Pr | H | H | O | CH$_2$CO$_2$Et |
| 2-270 | Pr | H | H | O | CHMeCO$_2$Me |
| 2-271 | Pr | H | H | O | CHMeCO$_2$Et |
| 2-272 | Pr | H | H | O | CHMeCO$_2$Pr |

TABLE 3

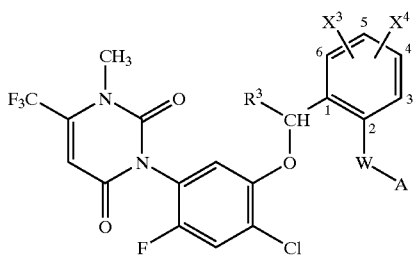

| Compound No. | $R^3$ | $X^3$ | $X^4$ | W | A |
|---|---|---|---|---|---|
| 3-1 | H | H | H | O | CHMeCO$_2$Me |
| 3-2 | H | H | H | O | CHMeCO$_2$Et |
| 3-3 | H | H | H | O | CHMeCO$_2$Pr |
| 3-4 | H | H | H | O | CHMeCO$_2$Bu |
| 3-5 | H | H | H | O | CHMeCO$_2$CHMe$_2$ |
| 3-6 | H | H | H | O | CHMeCO$_2$CMe$_3$ |
| 3-7 | H | H | H | O | CHMeCO$_2$CH$_2$CH$_2$F |
| 3-8 | H | H | H | O | CHMeCO$_2$CH$_2$CH$_2$Cl |
| 3-9 | H | H | H | O | CHMeCO$_2$CH$_2$CCl$_3$ |
| 3-10 | H | H | H | O | CHMeCO$_2$CH$_2$CH=CH$_2$ |
| 3-11 | H | H | H | O | CH$_2$CO$_2$Me |
| 3-12 | H | H | H | O | CH$_2$CO$_2$Et |
| 3-13 | H | H | H | O | CH$_2$CO$_2$Pr |
| 3-14 | H | H | H | O | CH$_2$CO$_2$Bu |
| 3-15 | H | H | H | O | CH$_2$CO$_2$CHMe$_2$ |
| 3-16 | H | H | H | O | CH$_2$CO$_2$CMe$_3$ |
| 3-17 | H | H | H | O | CH$_2$CO$_2$CH$_2$CH$_2$F |
| 3-18 | H | H | H | O | CH$_2$CO$_2$CH$_2$CH$_2$Cl |
| 3-19 | H | H | H | O | CH$_2$CO$_2$CH$_2$CCl$_3$ |
| 3-20 | H | H | H | O | CH$_2$CO$_2$CH$_2$CH=CH$_2$ |
| 3-21 | Me | H | H | O | CHMeCO$_2$Me |
| 3-22 | Me | H | H | O | CHMeCO$_2$Et |
| 3-23 | Me | H | H | O | CHMeCO$_2$Bu |
| 3-24 | Me | H | H | O | CHMeCO$_2$Pr |
| 3-25 | Me | H | H | O | CHMeCO$_2$CHMe$_2$ |
| 3-26 | Me | H | H | O | CHMeCO$_2$CMe$_3$ |
| 3-27 | Me | H | H | O | CHMeCO$_2$CH$_2$CH$_2$F |
| 3-28 | Me | H | H | O | CHMeCO$_2$CH$_2$CH$_2$Cl |
| 3-29 | Me | H | H | O | CHMeCO$_2$CH$_2$CCl$_3$ |
| 3-30 | Me | H | H | O | CHMeCO$_2$CH$_2$CH=CH$_2$ |
| 3-31 | Me | H | H | O | CH$_2$CO$_2$Me |
| 3-32 | Me | H | H | O | CH$_2$CO$_2$Et |
| 3-33 | Me | H | H | O | CH$_2$CO$_2$Pr |
| 3-34 | Me | H | H | O | CH$_2$CO$_2$Bu |
| 3-35 | Me | H | H | O | CH$_2$CO$_2$CHMe$_2$ |
| 3-36 | Me | H | H | O | CH$_2$CO$_2$CMe$_3$ |
| 3-37 | Me | H | H | O | CH$_2$CO$_2$CH$_2$CH$_2$F |
| 3-38 | Me | H | H | O | CH$_2$CO$_2$CH$_2$CH$_2$Cl |
| 3-39 | Me | H | H | O | CH$_2$CO$_2$CH$_2$CCl$_3$ |
| 3-40 | Me | H | H | O | CH$_2$CO$_2$CH$_2$CH=CH$_2$ |
| 3-41 | H | 3-Cl | H | O | CHMeCO$_2$Me |
| 3-42 | H | 3-Cl | H | O | CHMeCO$_2$Et |
| 3-43 | H | 3-Cl | H | O | CHMeCO$_2$Pr |
| 3-44 | H | 3-Cl | H | O | CHMeCO$_2$Bu |
| 3-45 | H | 3-Cl | H | O | CHMeCO$_2$CHMe$_2$ |
| 3-46 | H | 3-Cl | H | O | CHMeCO$_2$CMe$_3$ |
| 3-47 | H | 3-Cl | H | O | CHMeCO$_2$CH$_2$CH$_2$F |
| 3-48 | H | 3-Cl | H | O | CHMeCO$_2$CH$_2$CH$_2$Cl |
| 3-49 | H | 3-Cl | H | O | CHMeCO$_2$CH$_2$CCl$_3$ |
| 3-50 | H | 3-Cl | H | O | CHMeCO$_2$CH$_2$CH=CH$_2$ |
| 3-51 | H | 3-Cl | H | O | CH$_2$CO$_2$Me |
| 3-52 | H | 3-Cl | H | O | CH$_2$CO$_2$Et |
| 3-53 | H | 3-Cl | H | O | CH$_2$CO$_2$Pr |
| 3-54 | H | 3-Cl | H | O | CH$_2$CO$_2$Bu |
| 3-55 | H | 3-Cl | H | O | CH$_2$CO$_2$CHMe$_2$ |
| 3-56 | H | 3-Cl | H | O | CH$_2$CO$_2$CMe$_3$ |
| 3-57 | H | 3-Cl | H | O | CH$_2$CO$_2$CH$_2$CH$_2$F |
| 3-58 | H | 3-Cl | H | O | CH$_2$CO$_2$CH$_2$CH$_2$Cl |
| 3-59 | H | 3-Cl | H | O | CH$_2$CO$_2$CH$_2$CCl$_3$ |
| 3-60 | H | 3-Cl | H | O | CH$_2$CO$_2$CH$_2$CH=CH$_2$ |
| 3-61 | H | 3-OMe | H | O | CHMeCO$_2$Me |
| 3-62 | H | 3-OMe | H | O | CHMeCO$_2$Et |
| 3-63 | H | 3-OMe | H | O | CHMeCO$_2$Pr |
| 3-64 | H | 3-OMe | H | O | CHMeCO$_2$Bu |

TABLE 3-continued

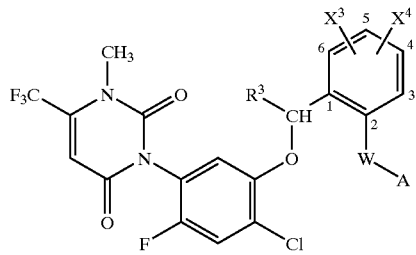

| Compound No. | $R^3$ | $X^3$ | $X^4$ | W | A |
|---|---|---|---|---|---|
| 3-65 | H | 3-OMe | H | O | $CHMeCO_2CHMe_2$ |
| 3-66 | H | 3-OMe | H | O | $CHMeCO_2CMe_3$ |
| 3-67 | H | 3-OMe | H | O | $CHMeCO_2CH_2CH_2F$ |
| 3-68 | H | 3-OMe | H | O | $CHMeCO_2CH_2CH_2Cl$ |
| 3-69 | H | 3-OMe | H | O | $CHMeCO_2CH_2CCl_3$ |
| 3-70 | H | 3-OMe | H | O | $CHMeCO_2CH_2CH=CH_2$ |
| 3-71 | H | 3-OMe | H | O | $CH_2CO_2Me$ |
| 3-72 | H | 3-OMe | H | O | $CH_2CO_2Et$ |
| 3-73 | H | 3-OMe | H | O | $CH_2CO_2Pr$ |
| 3-74 | H | 3-OMe | H | O | $CH_2CO_2Bu$ |
| 3-75 | H | 3-OMe | H | O | $CH_2CO_2CHMe_2$ |
| 3-76 | H | 3-OMe | H | O | $CH_2CO_2CMe_3$ |
| 3-77 | H | 3-OMe | H | O | $CH_2CO_2CH_2CH_2F$ |
| 3-78 | H | 3-OMe | H | O | $CH_2CO_2CH_2CH_2Cl$ |
| 3-79 | H | 3-OMe | H | O | $CH_2CO_2CH_2CCl_3$ |
| 3-80 | H | 3-OMe | H | O | $CH_2CO_2CH_2CH=CH_2$ |
| 3-81 | Me | 3-Cl | H | O | $CHMeCO_2Me$ |
| 3-82 | Me | 3-Cl | H | O | $CHMeCO_2Et$ |
| 3-83 | Me | 3-Cl | H | O | $CHMeCO_2Pr$ |
| 3-84 | Me | 3-Cl | H | O | $CHMeCO_2Bu$ |
| 3-85 | Me | 3-Cl | H | O | $CHMeCO_2CHMe_2$ |
| 3-86 | Me | 3-Cl | H | O | $CHMeCO_2CMe_3$ |
| 3-87 | Me | 3-Cl | H | O | $CHMeCO_2CH_2CH_2F$ |
| 3-88 | Me | 3-Cl | H | O | $CHMeCO_2CH_2CH_2Cl$ |
| 3-89 | Me | 3-Cl | H | O | $CHMeCO_2CH_2CCl_3$ |
| 3-90 | Me | 3-Cl | H | O | $CHMeCO_2CH_2CH=CH_2$ |
| 3-91 | Me | 3-Cl | H | O | $CH_2CO_2Me$ |
| 3-92 | Me | 3-Cl | H | O | $CH_2CO_2Et$ |
| 3-93 | Me | 3-Cl | H | O | $CH_2CO_2Pr$ |
| 3-94 | Me | 3-Cl | H | O | $CH_2CO_2Bu$ |
| 3-95 | Me | 3-Cl | H | O | $CH_2CO_2CHMe_2$ |
| 3-96 | Me | 3-Cl | H | O | $CH_2CO_2CMe_3$ |
| 3-97 | Me | 3-Cl | H | O | $CH_2CO_2CH_2CH_2F$ |
| 3-98 | Me | 3-Cl | H | O | $CH_2CO_2CH_2CH_2Cl$ |
| 3-99 | Me | 3-Cl | H | O | $CH_2CO_2CH_2CCl_3$ |
| 3-100 | Me | 3-Cl | H | O | $CH_2CO_2CH_2CH=CH_2$ |
| 3-101 | H | 4-Et | H | O | $CHMeCO_2Me$ |
| 3-102 | H | 4-Me | H | O | $CHMeCO_2Me$ |
| 3-103 | H | 4-Me | H | O | $CHMeCO_2Pr$ |
| 3-104 | H | 4-Me | H | O | $CHMeCO_2Bu$ |
| 3-105 | H | 4-Me | H | O | $CHMeCO_2CHMe_2$ |
| 3-106 | H | 4-Me | H | O | $CHMeCO_2CMe_3$ |
| 3-107 | H | 4-Me | H | O | $CHMeCO_2CH_2CH_2F$ |
| 3-108 | H | 4-Me | H | O | $CHMeCO_2CH_2CH_2Cl$ |
| 3-109 | H | 4-Me | H | O | $CHMeCO_2CH_2CCl_3$ |
| 3-110 | H | 4-Me | H | O | $CHMeCO_2CH_2CH=CH_2$ |
| 3-111 | H | 4-Me | H | O | $CH_2CO_2Me$ |
| 3-112 | H | 4-Me | H | O | $CH_2CO_2Et$ |
| 3-113 | H | 4-Me | H | O | $CH_2CO_2Pr$ |
| 3-114 | H | 4-Me | H | O | $CH_2CO_2Bu$ |
| 3-115 | H | 4-Me | H | O | $CH_2CO_2CHMe_2$ |
| 3-116 | H | 4-Me | H | O | $CH_2CO_2CMe_3$ |
| 3-117 | H | 4-Me | H | O | $CH_2CO_2CH_2CH_2F$ |
| 3-118 | H | 4-Me | H | O | $CH_2CO_2CH_2CH_2Cl$ |
| 3-119 | H | 4-Me | H | O | $CH_2CO_2CH_2CCl_3$ |
| 3-120 | H | 4-Me | H | O | $CH_2CO_2CH_2CH=CH_2$ |
| 3-121 | H | 4-OMe | H | O | $CHMeCO_2Me$ |
| 3-122 | H | 4-OMe | H | O | $CHMeCO_2Et$ |
| 3-123 | H | 4-OMe | H | O | $CHMeCO_2Pr$ |
| 3-124 | H | 4-OMe | H | O | $CHMeCO_2Bu$ |
| 3-125 | H | 4-OMe | H | O | $CHMeCO_2CHMe_2$ |
| 3-126 | H | 4-OMe | H | O | $CHMeCO_2CMe_3$ |
| 3-127 | H | 4-OMe | H | O | $CHMeCO_2CH_2CH_2F$ |
| 3-128 | H | 4-OMe | H | O | $CHMeCO_2CH_2CH_2Cl$ |

TABLE 3-continued

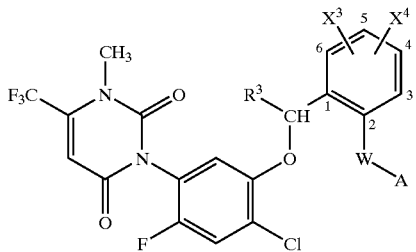

| Compound No. | $R^3$ | $X^3$ | $X^4$ | W | A |
| --- | --- | --- | --- | --- | --- |
| 3-129 | H | 4-OMe | H | O | $CHMeCO_2CH_2CCl_3$ |
| 3-130 | H | 4-OMe | H | O | $CHMeCO_2CH_2CH=CH_2$ |
| 3-131 | H | 4-OMe | H | O | $CH_2CO_2Me$ |
| 3-132 | H | 4-OMe | H | O | $CH_2CO_2Et$ |
| 3-133 | H | 4-OMe | H | O | $CH_2CO_2Pr$ |
| 3-134 | H | 4-OMe | H | O | $CH_2CO_2Bu$ |
| 3-135 | H | 4-OMe | H | O | $CH_2CO_2CHMe_2$ |
| 3-136 | H | 4-OMe | H | O | $CH_2CO_2CMe_3$ |
| 3-137 | H | 4-OMe | H | O | $CH_2CO_2CH_2CH_2F$ |
| 3-138 | H | 4-OMe | H | O | $CH_2CO_2CH_2CH_2Cl$ |
| 3-139 | H | 4-OMe | H | O | $CH_2CO_2CH_2CCl_3$ |
| 3-140 | H | 4-OMe | H | O | $CH_2CO_2CH_2CH=CH_2$ |
| 3-141 | H | 3-Cl | 5-Cl | O | $CHMeCO_2Me$ |
| 3-142 | H | 3-Cl | 5-Cl | O | $CHMeCO_2Et$ |
| 3-143 | H | 3-Cl | 5-Cl | O | $CHMeCO_2Pr$ |
| 3-144 | H | 3-Cl | 5-Cl | O | $CHMeCO_2Bu$ |
| 3-145 | H | 3-Cl | 5-Cl | O | $CHMeCO_2CHMe_2$ |
| 3-146 | H | 3-Cl | 5-Cl | O | $CHMeCO_2CMe_3$ |
| 3-147 | H | 3-Cl | 5-Cl | O | $CHMeCO_2CH_2CH_2F$ |
| 3-148 | H | 3-Cl | 5-Cl | O | $CHMeCO_2CH_2CH_2Cl$ |
| 3-149 | H | 3-Cl | 5-Cl | O | $CHMeCO_2CH_2CCl_3$ |
| 3-150 | H | 3-Cl | 5-Cl | O | $CHMeCO_2CH_2CH=CH_2$ |
| 3-151 | H | 3-Cl | 5-Cl | O | $CH_2CO_2Me$ |
| 3-152 | H | 3-Cl | 5-Cl | O | $CH_2CO_2Et$ |
| 3-153 | H | 3-Cl | 5-Cl | O | $CH_2CO_2Pr$ |
| 3-154 | H | 3-Cl | 5-Cl | O | $CH_2CO_2Bu$ |
| 3-155 | H | 3-Cl | 5-Cl | O | $CH_2CO_2CHMe_2$ |
| 3-156 | H | 3-Cl | 5-Cl | O | $CH_2CO_2CMe_3$ |
| 3-157 | H | 3-Cl | 5-Cl | O | $CH_2CO_2CH_2CH_2F$ |
| 3-158 | H | 3-Cl | 5-Cl | O | $CH_2CO_2CH_2CH_2Cl$ |
| 3-159 | H | 3-Cl | 5-Cl | O | $CH_2CO_2CH_2CCl_3$ |
| 3-160 | H | 3-Cl | 5-Cl | O | $CH_2CO_2CH_2CH=CH_2$ |
| 3-161 | H | 3-Cl | 5-Br | O | $CHMeCO_2Me$ |
| 3-162 | H | 3-Cl | 5-Br | O | $CHMeCO_2Et$ |
| 3-163 | H | 3-Cl | 5-Br | O | $CHMeCO_2Pr$ |
| 3-164 | H | 3-Cl | 5-Br | O | $CHMeCO_2Bu$ |
| 3-165 | H | 3-Cl | 5-Br | O | $CHMeCO_2CHMe_2$ |
| 3-166 | H | 3-Cl | 5-Br | O | $CHMeCO_2CMe_3$ |
| 3-167 | H | 3-Cl | 5-Br | O | $CHMeCO_2CH_2CH_2F$ |
| 3-168 | H | 3-Cl | 5-Br | O | $CHMeCO_2CH_2CH_2Cl$ |
| 3-169 | H | 3-Cl | 5-Br | O | $CHMeCO_2CH_2CCl_3$ |
| 3-170 | H | 3-Cl | 5-Br | O | $CHMeCO_2CH_2CH=CH_2$ |
| 3-171 | H | 3-Cl | 5-Br | O | $CH_2CO_2Me$ |
| 3-172 | H | 3-Cl | 5-Br | O | $CH_2CO_2Et$ |
| 3-173 | H | 3-Cl | 5-Br | O | $CH_2CO_2Pr$ |
| 3-174 | H | 3-Cl | 5-Br | O | $CH_2CO_2Bu$ |
| 3-175 | H | 3-Cl | 5-Br | O | $CH_2CO_2CHMe_2$ |
| 3-176 | H | 3-Cl | 5-Br | O | $CH_2CO_2CMe_3$ |
| 3-177 | H | 3-Cl | 5-Br | O | $CH_2CO_2CH_2CH_2F$ |
| 3-178 | H | 3-Cl | 5-Br | O | $CH_2CO_2CH_2CH_2Cl$ |
| 3-179 | H | 3-Cl | 5-Br | O | $CH_2CO_2CH_2CCl_3$ |
| 3-180 | H | 3-Cl | 5-Br | O | $CH_2CO_2CH_2CH=CH_2$ |
| 3-181 | H | H | H | O | $CH_2CH_2CH_2CO_2CH_3$ |
| 3-182 | H | H | H | O | $CHEtCO_2CH_3$ |
| 3-183 | H | H | H | O | $CH_2CH_2CH_2CH_2CO_2Me$ |
| 3-184 | Me | 3-Cl | 5-Br | O | $CHMeCO_2Me$ |
| 3-185 | Me | 4-Me | H | O | $CHMeCO_2Me$ |
| 3-186 | Me | 3-Cl | 5-Cl | O | $CHMeCO_2Me$ |
| 3-187 | H | 3-F | H | O | $CHMeCO_2Me$ |
| 3-188 | H | 3-Br | 5-Br | O | $CHMeCO_2Me$ |
| 3-189 | H | 5-$OCF_3$ | H | O | $CHMeCO_2Me$ |
| 3-190 | Me | 4-Me | H | O | $CHMeCO_2Me$ |
| 3-191 | Me | 4-Me | H | O | $CHMeCO_2Et$ |
| 3-192 | Me | 4-Me | H | O | $CHMeCO_2Pr$ |

TABLE 3-continued

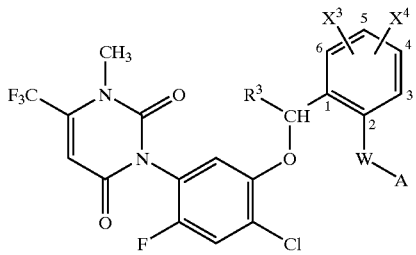

| Compound No. | $R^3$ | $X^3$ | $X^4$ | W | A |
|---|---|---|---|---|---|
| 3-193 | Me | 4-Me | H | O | $CHMeCO_2Bu$ |
| 3-194 | Me | 4-Me | H | O | $CHMeCO_2CHMe_2$ |
| 3-195 | Me | 4-Me | H | O | $CHMeCO_2CMe_3$ |
| 3-196 | Me | 4-Me | H | O | $CHMeCO_2CH_2CH_2F$ |
| 3-197 | Me | 4-Me | H | O | $CHMeCO_2CH_2CH_2Cl$ |
| 3-198 | Me | 4-Me | H | O | $CHMeCO_2CH_2CCl_3$ |
| 3-199 | Me | 4-Me | H | O | $CHMeCO_2CH_2CH{=}CH_2$ |
| 3-200 | Me | 4-Me | H | O | $CH_2CO_2Bu$ |
| 3-201 | Me | 4-Me | H | O | $CH_2CO_2Me$ |
| 3-202 | Me | 4-Me | H | O | $CH_2CO_2Et$ |
| 3-203 | Me | 4-Me | H | O | $CH_2CO_2Pr$ |
| 3-204 | Me | 4-Me | H | O | $CH_2CO_2CHMe_2$ |
| 3-205 | Me | 4-Me | H | O | $CH_2CO_2CMe_3$ |
| 3-206 | Me | 4-Me | H | O | $CH_2CO_2CH_2CH_2F$ |
| 3-207 | Me | 4-Me | H | O | $CH_2CO_2CH_2CH_2Cl$ |
| 3-208 | Me | 4-Me | H | O | $CH_2CO_2CH_2CCl_3$ |
| 3-209 | Me | 4-Me | H | O | $CH_2CO_2CH_2CH{=}CH_2$ |
| 3-210 | Et | H | H | O | $CH_2CO_2Me$ |
| 3-211 | Et | H | H | O | $CH_2CO_2Et$ |
| 3-212 | Et | H | H | O | $CH_2CO_2Pr$ |
| 3-213 | Et | H | H | O | $CHMeCO_2Me$ |
| 3-214 | Et | H | H | O | $CHMeCO_2Et$ |
| 3-215 | Et | H | H | O | $CHMeCO_2Pr$ |
| 3-216 | Et | H | H | O | $CH_2CO_2CH_2CH{=}CH_2$ |
| 3-217 | Et | H | H | O | $CHMeCO_2CH_2CH{=}CH_2$ |
| 3-218 | $CF_3$ | H | H | O | $CH_2CO_2Me$ |
| 3-219 | $CF_3$ | H | H | O | $CH_2CO_2Et$ |
| 3-220 | $CF_3$ | H | H | O | $CH_2CO_2Pr$ |
| 3-221 | $CF_3$ | H | H | O | $CHMeCO_2Me$ |
| 3-222 | $CF_3$ | H | H | O | $CHMeCO_2Et$ |
| 3-223 | $CF_3$ | H | H | O | $CHMeCO_2Pr$ |
| 3-224 | $CF_3$ | H | H | O | $CH_2CO_2CH_2CH{=}CH_2$ |
| 3-225 | $CF_3$ | H | H | O | $CHMeCO_2CH_2CH{=}CH_2$ |
| 3-226 | CN | H | H | O | $CHMeCO_2Me$ |
| 3-227 | CN | H | H | O | $CHMeCO_2Et$ |
| 3-228 | CN | H | H | O | $CHMeCO_2Pr$ |
| 3-229 | CN | H | H | O | $CHMeCO_2Bu$ |
| 3-230 | CN | H | H | O | $CHMeCO_2CHMe_2$ |
| 3-231 | CN | H | H | O | $CHMeCO_2CMe_3$ |
| 3-232 | CN | H | H | O | $CHMeCO_2CH_2CH_2F$ |
| 3-233 | CN | H | H | O | $CHMeCO_2CH_2CH_2Cl$ |
| 3-234 | CN | H | H | O | $CHMeCO_2CH_2CCl_3$ |
| 3-235 | CN | H | H | O | $CHMeCO_2CH_2CH{=}CH_2$ |
| 3-236 | CN | H | H | O | $CH_2CO_2Me$ |
| 3-237 | CN | H | H | O | $CH_2CO_2Et$ |
| 3-238 | H | 4-Et | H | O | $CHMeCO_2Et$ |
| 3-239 | H | 4-Et | H | O | $CHMeCO_2Pr$ |
| 3-240 | H | 4-Et | H | O | $CHMeCO_2Bu$ |
| 3-241 | H | 4-Et | H | O | $CHMeCO_2CHMe_2$ |
| 3-242 | H | 4-Et | H | O | $CH_2CO_2Me$ |
| 3-243 | H | 4-Et | H | O | $CH_2CO_2Et$ |
| 3-244 | H | 4-Et | H | O | $CH_2CO_2Pr$ |
| 3-245 | H | 4-Et | H | O | $CH_2CO_2CHMe_2$ |
| 3-246 | Ph | H | H | O | $CHMeCO_2Me$ |
| 3-247 | Ph | H | H | O | $CHMeCO_2Et$ |
| 3-248 | Ph | H | H | O | $CHMeCO_2CH_2CH_2CH_3$ |
| 3-249 | Ph | H | H | O | $CH_2CO_2Me$ |
| 3-250 | Ph | H | H | O | $CH_2CO_2Et$ |
| 3-251 | H | H | H | S | $CHMeCO_2Me$ |
| 3-252 | H | H | H | S | $CHMeCO_2Et$ |
| 3-253 | H | H | H | S | $CHMeCO_2Pr$ |
| 3-254 | H | H | H | S | $CHMeCO_2Bu$ |
| 3-255 | H | H | H | S | $CHMeCO_2CHMe_2$ |
| 3-256 | H | H | H | S | $CHMeCO_2CMe_3$ |

TABLE 3-continued

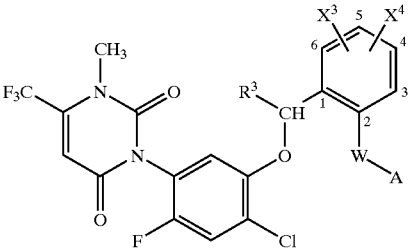

| Compound No. | R³ | X³ | X⁴ | W | A |
|---|---|---|---|---|---|
| 3-257 | H | H | H | S | CHMeCO$_2$CH$_2$CH$_2$F |
| 3-258 | H | H | H | S | CHMeCO$_2$CH$_2$CH$_2$Cl |
| 3-259 | H | H | H | S | CHMeCO$_2$CH$_2$CCl$_3$ |
| 3-260 | H | H | H | S | CHMeCO$_2$CH$_2$CH=CH$_2$ |
| 3-261 | H | H | H | S | CH$_2$CO$_2$Me |
| 3-262 | H | H | H | S | CH$_2$CO$_2$Et |
| 3-263 | H | H | H | S | CH$_2$CO$_2$Pr |
| 3-264 | H | H | H | S | CH$_2$CO$_2$Bu |
| 3-265 | H | H | H | S | CH$_2$CO$_2$CHMe$_2$ |
| 3-266 | H | H | H | S | CH$_2$CO$_2$CMe$_3$ |
| 3-267 | H | H | H | S | CH$_2$CO$_2$CH$_2$CH$_2$F |
| 3-268 | H | H | H | S | CH$_2$CO$_2$CH$_2$CH$_2$Cl |
| 3-269 | H | H | H | S | CH$_2$CO$_2$CH$_2$CCl$_3$ |
| 3-270 | H | H | H | S | CH$_2$CO$_2$CH$_2$CH=CH$_2$ |
| 3-271 | Me | H | H | S | CHMeCO$_2$Me |
| 3-272 | Me | H | H | S | CHMeCO$_2$Et |
| 3-273 | Me | H | H | S | CHMeCO$_2$Pr |
| 3-274 | Me | H | H | S | CH$_2$CO$_2$Me |
| 3-275 | Me | H | H | S | CH$_2$CO$_2$Et |
| 3-276 | Pr | H | H | O | CH$_2$CO$_2$Me |
| 3-277 | Pr | H | H | O | CH$_2$CO$_2$Et |
| 3-278 | Pr | H | H | O | CH$_2$CO$_2$Pr |
| 3-279 | Pr | H | H | O | CH$_2$CO$_2$CHMe$_2$ |
| 3-280 | Pr | H | H | O | CH$_2$CO$_2$CMe$_3$ |
| 3-281 | Pr | H | H | O | CH$_2$CO$_2$CH$_2$CH$_2$F |
| 3-282 | Pr | H | H | O | CH$_2$CO$_2$CH$_2$CH$_2$Cl |
| 3-283 | Pr | H | H | O | CH$_2$CO$_2$CH$_2$CCl$_3$ |
| 3-284 | Pr | H | H | O | CH$_2$CO$_2$CH$_2$CH=CH$_2$ |

(in these tables, "Me" represents methyl, "Et" represents ethyl, "Pr" represents propyl, "Bu" represents butyl, and "Ph" represents phenyl.)

Next, formulation examples of the compounds of the invention are described. Compound numbers for the compounds of the invention are represented the Numbers appeared in Table 1 to 3 described above, and "part(s)" represents "part(s) by weight".

Formulation Example 1

Fifty (50) parts of each of compounds 1-1 to 1-284, 2-1 to 2-272, and 3-1 to 3-284, 3 parts of calcium ligninsulfonate, 2 parts of sodium laurylsulfate, and 45 parts of synthetic hydrated silica are well pulverized and mixed, to separately obtain wettable powders of each compound.

Formulation Example 2

Ten (10) parts of each of compounds 1-1 to 1-284, 2-1 to 2-272, and 3-1 to 3-284, 14 parts of polyoxyethylenestyryl phenyl ether, 6 parts of calcium dodecylbenzenesulfonate, 35 parts of xylene, and 35 parts of cyclohexanone are well mixed to separately obtain emulsifiable concentrates of each compound.

Formulation Example 3

Two (2) parts of each of compounds 1-1 to 1-284, 2-1 to 2-272, and 3-1 to 3-284, 2 parts of synthetic hydrated silica, 2 parts of calcium ligninsulfonate, 30 parts of bentonite, and 64 parts of kaolin clay are well pulverized and mixed. After adding water and well kneading, the mixtures are granulated and dried to separately obtain granules of each compound.

Formulation Example 4

Twenty-five (25) parts of each of compounds 1-1 to 1-284, 2-1 to 2-272, and 3-1 to 3-284, 50 parts of a 10% aqueous solution of polyvinyl alcohol, and 25 parts of water are mixed, and are wet pulverized until the average particle diameter is 5 μm or less, to separately obtain flowables of each compound.

Formulation Example 5

Five(S) parts of each of compounds 1-1 to 1-284, 2-1 to 2-272, and 3-1 to 3-284 is added into 40 parts of 10% aqueous solution of polyvinyl alcohol, and the mixture is emulsified and dispersed until the average diameter is 10 μm or less by homogenizer. Next, 55 parts of water is added to the resultant mixture to separately obtain concentrated emulsions of each compound.

Next, test examples are explained to show that the compounds of the invention are effective as an active ingredient of a herbicide. In the examples, the compounds are identified by the Compound Numbers as in Tables 1 to 3. The herbicidal effect in the tests is evaluated at 11 levels with indices of 0 to 10, i.e., shown by numeral "0", "1", "2", "3", "4", "5", "6", "7", "8", "9" or "10", wherein "0" means that little difference in the degree of germination or growth between the treated plants and the untreated plants at the time of examination, and "10" means that the treated plants died completely or their germination or growth was completely inhibited.

Test Example 1

Test for Foliar Treatment on Upland Field

A cylindrical plastic pot having a diameter of 10 cm and a depth of 10 cm was filled with soil and seeded with ivyleaf momingglory, velvetleaf and bamyardgrass. These test plants were grown in a greenhouse for 9 days. Then each of compounds 1-1, 2-1, 2-2, 3-1 and 3-101 was formulated into an emulsifiable concentrate according to Formulation Example 2 and then diluted to the prescribed amount with water containing a spreading agent and the dilution was uniformly sprayed over the foliage of the test plants with sprayer at a rate of 1000 liters per hectare. After the application, the test plants were grown in the greenhouse for 8 days, and the herbicidal activity were determined. As a result, the growth of ivyleaf momingglory, velvetleaf and barnyardgrass were completely controlled when compounds 1-1, 2-1, 2-2, 3-1 and 3-101 were applied at the dosage of 125 g/ha, respectively.

Test Example 2

Test for Soil Surface Treatment on Upland Field

A cylindrical plastic pot having a diameter of 10 cm and a depth of 10 cm was filled with soil and seeded with velvetleaf. Then each of compounds 1-1, 2-1, 2-2, 3-1 and 3-101 was formulated into an emulsifiable concentrate according to Formulation Example 2 and then diluted to the prescribed amount with water and dilution was uniformly sprayed over the surface of the soil with sprayer at a rate of 1000 liters per hectare. After the application, the test plants were grown in a greenhouse for 12 days, and the herbicidal activity was examined. As a result, the germination of velvetleaf was completely controlled when compounds 1-1, 2-1, 2-2, 3-1 and 3-101 were applied at the dosage of 500 g/ha, respectively.

Test Example 3

Test for Foliar Treatment on Upland Field

A cylindrical plastic pot having a diameter of 10 cm and a depth of 10 cm was filled with soil and seeded with ivyleaf momingglory, velvetleaf and barnyardgrass. These test plants were grown in a greenhouse for 10 days. Then each of compounds listed below was formulated into an emulsifiable concentrate according to Formulation Example 2 and then diluted to the prescribed amount with water containing a spreading agent and the dilution was uniformly sprayed over the foliage of the test plants with sprayer at a rate of 1000 liters per hectare. After the application, the test plants were grown in the greenhouse for 16 days, and the herbicidal activity were determined. The results are shown in Table 4.

TABLE 4

| Test compound | Dosage of an active ingredient (g/ha) | Herbicidal effect | | |
|---|---|---|---|---|
| | | Ivyleaf morning-glory | Velvetleaf | Barnyard-grass |
| 1-1 | 125 | 10 | 10 | 10 |
| 1-2 | 125 | 10 | 10 | 10 |
| 1-21 | 125 | 10 | 10 | 10 |
| 1-42 | 125 | 10 | 10 | 10 |
| 1-61 | 125 | 10 | 10 | 10 |
| 1-101 | 125 | 10 | 10 | 10 |
| 1-161 | 125 | 10 | 10 | 8 |
| 1-213 | 125 | 10 | 10 | 10 |
| 1-226 | 125 | 10 | 10 | 10 |
| 1-238 | 125 | 10 | 10 | 9 |
| 1-242 | 125 | 10 | 10 | 10 |
| 1-246 | 125 | 10 | 10 | 8 |
| 2-1 | 125 | 10 | 10 | 10 |
| 2-2 | 125 | 10 | 10 | 10 |
| 2-11 | 125 | 10 | 10 | 8 |
| 2-21 | 32 | 10 | 10 | 10 |
| 2-41 | 125 | 10 | 10 | 10 |
| 2-61 | 125 | 10 | 10 | 10 |
| 2-101 | 125 | 10 | 10 | 10 |
| 2-161 | 125 | 10 | 10 | 10 |
| 2-187 | 125 | 10 | 10 | 10 |

Test Example 4

Test for Soil Surface Treatment on Upland Field

A cylindrical plastic pot having a diameter of 10 cm and a depth of 10 cm was filled with soil and seeded ivyleaf momingglory, velvetleaf and barnyardgrass. Then each of compounds listed below was formulated into an emulsifiable concentrate according to Formulation Example 2 and then diluted to the prescribed amount with water and dilution was uniformly sprayed over the surface of the soil with sprayer at the rate of 1000 liters per hectare. After the application, the test plants were grown in a greenhouse for 12 days, and the herbicidal activity was examined. The results are shown in Table 5.

TABLE 5

| Test compound | Dosage of an active ingredient (g/ha) | Herbicidal effect | | |
|---|---|---|---|---|
| | | Ivyleaf morning-glory | Velvetleaf | Barnyard-grass |
| 1-1 | 500 | 10 | 10 | 9 |
| 1-2 | 500 | 10 | 10 | 10 |
| 1-21 | 500 | 10 | 10 | 10 |
| 1-42 | 500 | 10 | 10 | 8 |
| 1-61 | 500 | 10 | 10 | 10 |
| 1-101 | 500 | 10 | 10 | 10 |
| 1-161 | 500 | 7 | 10 | 4 |
| 1-213 | 500 | 10 | 10 | 10 |
| 1-226 | 500 | 10 | 10 | 9 |
| 1-238 | 500 | 10 | 10 | 8 |
| 1-242 | 500 | 10 | 10 | 10 |
| 1-246 | 500 | 8 | 10 | 10 |
| 2-1 | 500 | 10 | 10 | 10 |
| 2-2 | 500 | 10 | 10 | 10 |
| 2-11 | 500 | 10 | 10 | 9 |
| 2-21 | 500 | 10 | 10 | 10 |
| 2-41 | 500 | 10 | 10 | 10 |
| 2-61 | 500 | 10 | 10 | 10 |
| 2-101 | 500 | 10 | 10 | 10 |

TABLE 5-continued

| Test compound | Dosage of an active ingredient (g/ha) | Herbicidal effect Ivyleaf morning-glory | Velvetleaf | Barnyard-grass |
|---|---|---|---|---|
| 2-161 | 500 | 6 | 10 | 5 |
| 2-187 | 500 | 10 | 10 | 9 |

Test Example 5

Test for Foliar Treatment on Upland Field

A pot for plug seedlings seeded with large crabgrass. The test plant was grown in a greenhouse for 14 days, then transplanted into a plastic pot having an area of 17×12 cm² and a depth of 7 cm, and further the test plants were grown in the greenhouse for 8 days. Then each of compounds listed below was formulated into an emulsifiable concentrate according to Formulation Example 2 and then diluted to the prescribed amount with water containing a spreading agent and the dilution was uniformly sprayed over the foliage of the test plants with sprayer at a rate of 1000 liters per hectare. After the application, the test plants were grown in the greenhouse for 19 days, and the herbicidal activity were determined. The results are shown in Table 6.

TABLE 6

| Test Compound | Dosage of an active ingredient (g/ha) | Herbicidal effect Large crabgrass |
|---|---|---|
| 1-1 | 125 | 10 |
| 1-2 | 125 | 10 |
| 1-21 | 125 | 10 |
| 1-42 | 125 | 10 |
| 1-61 | 125 | 10 |
| 1-101 | 125 | 10 |
| 1-161 | 125 | 10 |
| 1-213 | 125 | 10 |
| 1-226 | 125 | 10 |
| 1-238 | 125 | 10 |
| 1-242 | 125 | 10 |
| 1-246 | 125 | 10 |
| 2-1 | 125 | 10 |
| 2-2 | 125 | 10 |
| 2-11 | 125 | 10 |
| 2-21 | 125 | 10 |
| 2-41 | 125 | 10 |
| 2-61 | 125 | 10 |
| 2-101 | 125 | 10 |
| 2-161 | 125 | 10 |
| 2-187 | 125 | 10 |

Test Example 6

Test for Foliar Treatment on Upland Field

A plastic pot having a area of 27×20 cm² and a depth of 7.5 cm filled with soil, seeded with barnyardgrass. The test plant was grown in a greenhouse for 4 days. The seedlings of large crabgrass and giant foxtail, which were seeded into a pot for plug seedlings and grown in a greenhouse for 14 days, were transplanted into the plastic pot. The test plants, further, were grown in the greenhouse for 8 days. Then each of compound listed below was formulated into an emulsifiable concentrate according to Formulation Example 2 and then diluted to the prescribed amount with water containing a spreading agent and the dilution was uniformly sprayed over the foliage of the test plants with sprayer at a rate of 1000 liters per hectare. After the application, the test plants were grown in the greenhouse for 19 days, and the herbicidal activity were determined. The results are shown in Table 7.

TABLE 7

| Test compound | Dosage of an active ingredient (g/ha) | Herbicidal effect Large crabgrass | Giant foxtail | Barnyard-grass |
|---|---|---|---|---|
| 1-1 | 8 | 10 | 9 | 10 |
| 2-1 | 8 | 10 | 10 | 10 |

Industrial Applicability

Applying the compound of the invention results excellent herbicidal effect.

What is claimed is:

1. An uracil compound represented by the general formula:

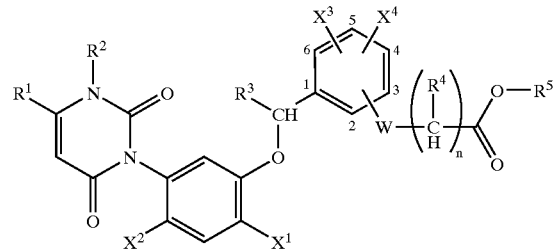

wherein W represents oxygen or sulfur; $R^1$ represents $C_1$- to $C_3$-alkyl or $C_1$- to $C_3$-haloalkyl; $R^2$ represents $C_1$- to $C_3$-alkyl or $C_1$- to $C_3$-haloalkyl; $R^3$ represents hydrogen, $C_1$- to $C_3$-alkyl, phenyl, $C_1$- to $C_3$-haloalkyl or cyano; $R^4$ represents hydrogen or $C_1$- to $C_3$-alkyl; $R^5$ represents $C_1$- to $C_6$-alkyl, $C_1$- to $C_6$-haloalkyl, $C_3$- to $C_6$-alkenyl, $C_3$- to $C_6$-haloalkenyl, $C_3$- to $C_6$-alkynyl or $C_3$- to $C_6$-haloalkynyl; $X^1$ represents halogen; $X^2$ represents hydrogen or halogen; $X^3$ and $X^4$ are independent with each other and each represents hydrogen, halogen, $C_1$- to $C_6$-alkyl, $C_1$- to $C_6$-haloalkyl, $C_2$- to $C_6$-alkenyl, $C_2$- to $C_6$-haloalkenyl, $C_3$- to $C_6$-alkynyl, $C_3$- to $C_6$-haloalkynyl, $C_1$- to $C_6$-alkoxy-$C_1$- to $C_6$-alkyl, $C_1$- to $C_6$-alkoxy, $C_1$- to $C_6$-haloalkoxy or cyano; and n represents an integer of 1 to 4.

2. The uracil compound according to claim 1, wherein $X^1$ is chlorine.

3. The uracil compound according to claim 1 or 2, wherein $X^2$ is hydrogen or fluorine.

4. The uracil compound according to claim 1, wherein $R^1$ is methyl or $CF_3$.

5. The uracil compound according to claim 1, wherein W is oxygen.

6. The uracil compound according to claim 1 or 5, wherein $R^4$ is methyl and n is 1.

7. The uracil compound according to claim 1 or 4, wherein $R^2$ is methyl.

8. The uracil compound according claim 1, wherein $R^3$ is hydrogen.

9. The uracil compound according to claim 1, wherein R is $C_1$- to $C_3$-alkyl, phenyl, $C_1$- to $C_3$-haloalkyl or cyano.

10. The uracil compound according to claim 1, wherein $X^3$ and $X^4$ are hydrogen.

11. The uracil compound according to claim 1, wherein the connecting position of W is 3-position or 4-position on the benzene ring.

12. A herbicide comprising the uracil compound according to claim 1 as an active ingredient, and an inert carrier.

13. A method for controlling weeds, which comprises applying a herbicidally effective amount of the uracil compound according to claim 1, to weeds or a place where weeds are growing or will grow.

* * * * *